(12) United States Patent
Meltzer et al.

(10) Patent No.: US 6,562,589 B1
(45) Date of Patent: May 13, 2003

(54) AIB1, A NOVEL STEROID RECEPTOR CO-ACTIVATOR

(75) Inventors: Paul Meltzer, Rockville, MD (US); Jeffrey Trent, Paradise Valley, AZ (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/125,635

(22) PCT Filed: Jun. 17, 1998

(86) PCT No.: PCT/US98/12689

§ 371 (c)(1),
(2), (4) Date: Aug. 21, 1998

(87) PCT Pub. No.: WO98/57982

PCT Pub. Date: Dec. 23, 1998

Related U.S. Application Data

(60) Provisional application No. 60/049,728, filed on Jun. 17, 1997.

(51) Int. Cl.$^7$ .......................... C07H 21/04; C12N 15/12; C12N 15/63; C07K 14/00

(52) U.S. Cl. .......................... 435/69.1; 6/7.1; 6/172.3; 6/235; 6/320.1; 6/325; 6/252.3; 536/23.5; 536/24.3; 536/23.1; 536/23.4; 530/300; 530/350

(58) Field of Search .......................... 435/69.1, 320.1, 435/325, 252.3, 172.3, 6, 7.1, 235.1; 536/23.5, 24.3, 23.1, 23.4; 530/300, 350

(56) References Cited

U.S. PATENT DOCUMENTS

| | | | |
|---|---|---|---|
| 5,028,525 A | 7/1991 | Gray et al. | ..................... 435/6 |
| 5,447,841 A | 9/1995 | Gray et al. | ..................... 435/6 |
| 5,472,842 A | 12/1995 | Stokke et al. | .................. 435/6 |
| 5,506,102 A | 4/1996 | McDonnell | ..................... 435/6 |
| 5,639,592 A | 6/1997 | Evans et al. | .................... 435/4 |
| 5,716,595 A | 2/1998 | Goldenberg | ............... 414/1.49 |

FOREIGN PATENT DOCUMENTS

| | | |
|---|---|---|
| WO | WO 97/10337 | 3/1997 |
| WO | WO 97/35195 | 9/1997 |

OTHER PUBLICATIONS

Anzick et al., AIB1, a Steroid Receptor Coactivator Amplified in Breast and Ovarian Cancer, *Science* 277:965–968 (1997).

Brünner et al., Acquisition of Hormone–Independent Growth in MCF–7 Cells Is Accompanied by Increased Expression of Estrogen–Regulated Genes but Without Detectable DNA Amplifications, *Cancer Research* 53:283–290 (1993).

Chen et al., Nuclear Receptor Coactivator ACTR Is a Novel Histone Acetyltransferase and Forms a Multimeric Activation Complex with P/CAF and CBP/p300, *Cell* 90:569–580 (1997).

Courjal et al., Mapping of DNA Amplifications at 15 Chromosomal Localizations in 1875 Breast Tumors: Definition of Phenotypic Groups, *Cancer Research* 57:4360–4367 (1997).

Ding et al., Nuclear Receptor–Binding Sites of Coactivators Glucocorticoid Receptor Interacting Protein 1 (GRIP1) and Steroid Receptor Coactivator 1 (SRC–1): Multiple Motifs with Different Binding Specificities, *Molecular Endocrinology* 12:302–313 (1998).

Guan et al., Identification of Cryptic Sites of DNA Sequence Amplification in Human Breast Cancer by Chromosome Microdissection, Nature Genetics 8:155–161 (1994).

Guan et al., Hybrid Selection of Transcribed Sequences from Microdissected DNA Isolation of Genes Within an Amplified Region at 20q11–q13.2 in *Breast Cancer*, Cancer Research 56:3446–3450 (1996).

Ito et al., Steroidogenic Factor–1 Contains a Carboxy–Terminal Transcriptional Activation Domain That Interacts with Steroid Receptor Coactivator–1, *Molecular Endocrinology* 12:290–301 (1998).

Kalkhoven et al., Isoforms of Steroid Receptor Co–activator 1 Differ in Their Ability to Potentiate Transcription by the Estrogen Receptor, *The EMBO Journal* 17:232–243 (1998).

Kallioniemi et al., Detection and Mapping of Amplified DNA Sequences in Breast Cancer by Comparative Genomic Hybridization, *Proc. Natl. Acad. Sci. USA* 91:2156–2160 (1994).

Kliewer et al., An Orphan Nuclear Receptor Activated by Pregnanaes Defines a Novel Steroid Signaling Pathway, *Cell* 92:73–82 (1998).

Kraus, W.L. and Kadonaga, J.T., p300 and Estrogen Receptor Cooperatively Activate Transcription Via Differential Enhancement of Initiation and Reinitiation, *Genes & Development* 12:331–342 (1998).

Li, H. and Chen, J.D., The Receptor–Associated Coactivator 3 Activates Transcription Through CREB–Binding Protein Recruitment and Autoregulation, *The Journal of Biological Chemistry* 273:5948–5954 (1998).

Li et al., RAC3, a Steroid/Nuclear Receptor–Associated Coactivator That Is Releated to SRC–1 and TIF2, *Proc. Natl. Acad. Sci, USA* 94:8479–8484 (1997).

(List continued on next page.)

Primary Examiner—Yvonne Eyler
Assistant Examiner—Nirmal S. Basi
(74) Attorney, Agent, or Firm—Klarquist Sparkman, LLP

(57) ABSTRACT

The invention features a substantially pure DNA which includes a sequence encoding a novel steroid receptor co-activator which is overexpressed in breast cancer cells, diagnostic assays for steroid hormone-responsive cancers, and screening assays to identify compounds which inhibit an interaction of the co-activator with the steroid hormone.

30 Claims, 8 Drawing Sheets

OTHER PUBLICATIONS

Onate et al., Sequence and Characterization of a Coactivator of the Steroid Hormone Receptor Superfamily, *Science* 270:1354–1357 (1995).

Sluyser M., Role of Estrogen Receptor Variants in the Development of Hormone Resistance in Breast Cancer, *Clinical Biochemistry* 25:407–414 (1992).

Takeshita et al., TRAM–1, a Novel 160–kDa Thyroid Hormone Receptor Activator Molecule, Exhibits Distinct Properties from Steroid Receptor Coactivator–1, *The Journal of Biological Chemistry* 272:27629–27634 (1997).

Tanner et al., Amplification of Chromosomal Region 20q13 in Invasive Breast Cancer: Prognostic Implicaitons, *Clinical Cancer Research* 1:1455–1461 (1995).

Torchia et al., The Transcriptional Co–activator p/CIP Binds CBP and Mediates Nuclear–Receptor Function, *Nature* 387:677–684 (1997).

Tremblay et al., Ligand–Independent Activation of the Estrogen Receptors $\alpha$ and $\beta$ by Mutations of a Conserved Tyrosine Can Be Abolished by Antiestrogens,*Cancer Research* 58:877–881 (1998).

Voegel et al., TIF2, a 160 kDa Transcriptional Mediator for the Ligand–Dependent Activation Function AF–2 of Nuclear Receptors, The EMBO Journal 15:3667–3675 (1996).

Xu et al., Partial Hormone Resistance in Mice with Disruption of the Steroid Receptor Coactivator –1 (SRC–1) Gene, *Science* 279:1922–1925 (1998).

Yeh, S. and Chang, C., Cloning and Characterization of a Specific Coactivator, $ARA_{70}$, for the Androgen Receptor in Human Prostate Cells, *Proc. Natl. Acad. Sci. USA* 93:5517–5521 (1996).

FIGURE 5A: MOUSE AIB1 (pCIP) INTRON/EXON BOUNDARIES

| Exon | cDNA bp 5'exon | cDNA bp 3'exon | 3'intron splice site | Exon sequence (5' to 3') | 5'intron splice site |
|---|---|---|---|---|---|
| 1 | | 11 | | GGCGGCGAACG | |
| 2 | 12 | | | GATCAAAAGAATTTGCTGAA | |
| 2 | | 90 | TGTCACCTCTTCTTCCGCAG | CCTTCCTGAACAGCTGTCAG | |
| 3 | 91 | | | TTGCTGATCTGTGATCAGGA | |
| 3 | | 195 | GGCTTTTCTCCGCCCTTCCAG | TGTGATGCCCCAGGACAGGG | |
| 4 | 196 | | | GCTTGTCTACAGTGGTGAGA | |
| 4 | | 368 | GCTTCCTTCTGTGTCTTCAG | ACGGCAAATAAAGAACAAG | GTAACACAGAGTCAGAAAAA |
| 5 | 369 | | | GAAAACTATTTCCAGTGAT | |
| 5 | | 469 | ATTAACACATTCCACTGTAG | TAGGACCGCTTTTACTACAG | ATTTTCTTACAAACGAGGCT |
| 6 | 470 | | | GCACTGGATGGTTTCCTGTT | |
| 6 | | 644 | TTTTAATTGTTTTCAAAG | ACACTTACCAAAATCCACAG | GTGGGCTCTTCTTTGTGTT |
| 7 | 645 | | | TTAATGGAGTTTCTTGGACT | |
| 7 | | 830 | CTGGTGACCTTTCGTTGTAG | TATGCTGGAAGAGGAGAAG | GTGAGAGGCGGGTCCACTGT |
| 8 | 831 | | | ACTTGCAGTGCTGTATGATC | |
| 8 | | 923 | TCTGTTTTATCTTTAATAG | TACCAGACATGACCTTTCCG | GTAAGACCAGTCTTCACTGG |
| 9 | 924 | | | GAAAGGTTGTCAATATAGAT | |
| 9 | | 1064 | GTGTGCTTCCCCCTCCGTAG | GAAGCGTCACTATCAAGAAG | GTGAGGGAGGCGTTTGGGGT |
| 10 | 1065 | | | CTTATGTTCATGGCCACGCA | |
| 10 | | 1212 | TTGCGTGTGTTGTTTGCAG | TCGACCCACTTCTTCAGAG | GTGATGACACTAAAGCACCC |
| 11 | 1213 | | | AGAACAGAATGGATACAGAC | |
| 11 | | 1589 | CGACCTTTCTCCATATGCAG | CCAGTTCTCTCCTGCTGCAG | GTATCCACAGCTGCGTTTTC |
| 12 | 1590 | | | GTGCACACTCACCCATGGGA | |
| 12 | | 2458 | TTTAAAGGTTCATTTTCAG | AGACCGAGACGAACGAGGAG | GAGGTAAGGTACTCTCTGTT |
| 13 | 2459 | | | GTATCGGGAGACCTGGATAA | |
| 13 | | 2588 | AGCTTCTGTGTTTCAACAG | TGCAGGACCGAGTTCTCTGG | GTAAGGAAAACCAGAGTTTT |
| 14 | 2589 | | | GTTTGCGAAGTCCACAGCCT | |
| 14 | | 2783 | | GAATTACGGTGCCAACATGG | GTAGGTCATGTCTAAGTGTG |

FIGURE 5B: MOUSE AIB1 (pCIP) INTRON/EXON BOUNDARIES

| Exon | cDNA bp 5'exon | cDNA bp 3'exon | 3'intron splice site | Exon sequence (5' to 3') | | 5'intron splice site |
|---|---|---|---|---|---|---|
| 15 | 2784 | | TGAGCCCTCCCTAATTTTAG | GCCCAAACAGAAATGTTCCT | GCAGCAGATGCTTCAAATGA | GTAAGCTGTCCCTTTCAATA |
| 15 | | 3095 | | | | |
| 16 | 3096 | | ATTTTGATTTGCTCCCCCAG | GAACTGGTGAGATTCCCATG | CCTCACGGGTCTCAAAATAG | GTAGGGTTTATTTTGGGAT |
| 16 | | 3222 | | | | |
| 17 | 3223 | | TGACTCACGTCTCTCTCTAG | GCCTCTTCTTAGAAACTCTC | TTCCTGAGCTCGTGAATCAG | GTGGAGTTGCAATCTGTGAG |
| 17 | | 3394 | | | | |
| 18 | 3395 | | CTTTGTGTTTGATGTTTAAG | GGACAAGCTTTGGAGTCCAA | AGAGGCTACAGGGCCAGCAG | GTAAGACCGGGCTGTCAGGG |
| 18 | | 3688 | | | | |
| 19 | 3689 | | ACTAACCCAACTCTGTTCAG | TTTTAAATCAGAGCCGGCA | TGAGGCCCATGATGCCCCAG | GTACGTTCCCTGCAGAGAAG |
| 19 | | 3772 | | | | |
| 20 | 3773 | | TGTCTCTTGGCTACCAGCAG | GCTTTCTTTAATGCCCAAAT | TCCATATCCAGCAAATTACG | GTAAACCTGTCAGATTGTGC |
| 20 | | 3989 | | | | |
| 21 | 3990 | | TTTCTGTTCATTTCTTTAAG | GAATGGGACAACCACCAGAG | GGGAACCTGGCCAGGAATGG | GTAAGGATGGGACTTACTTT |
| 21 | | 4164 | | | | |
| 22 | 4165 | | CTGTTACCCTTTCTTTGCAG | CTCCTTCCCCCAGCAGCAGT | TGCCCATGGGCCCCGATCAG | GTACGGGCATCTATTCTTAC |
| 22 | | 4306 | | | | |
| 23 | 4307 | | CTGTGTTCTTCTGTTAACAG | AAATACTGCTGACATCTCCC | | |
| 23 | | 4622 | | | | |

FIGURE 6A: HUMAN AIB1 INTRON/EXON BOUNDARIES

| Exon | cDNA bp 5'exon | cDNA bp 3'exon | 3'intron splice site | Exon sequence (5' to 3') | 5'intron splice site |
|---|---|---|---|---|---|
| 1 | | 102 | | GAGGAAAATGGCGGCGGGAG | GTGAGTGGAGATAAAGGAGG |
| 2 | 103 | 181 | CCTCTTCTTTTTGTCCCTCAG GATCAAATACTTGCTGGAT | TCCTTTGACTGGTTAGCCAG | GTAATTCAGCTTTAGTTTGA |
| 2 3 | 182 | 283 | TTCTCATTATTCTCTCTTAG TTGCTGATGTATATTCAAGA | TGTGATACTCCAGGACAAGG | GTAGGTGACTTATTTCCTGG |
| 3 4 | 284 | 456 | TTCTACGCCTTTTCCCTTAG TCTTACCTGCAGTGGTGAAA | ACGTCAAATAAAAGAGCAAG | GTAATAAAAACACTCATGTC |
| 4 5 | 457 | 557 | ACCACCTTCTGTCTTTTCAG GAAAACTATTTCCAATGAT | TAGGACCGCTTTACTTCAG | GCAAGTATAAAGATTTTAAC |
| 5 6 | 558 | 732 | ATTAACATATCCTATTTTAG GCATTGGATGGTTTCCTATT | GAATTTACCAAAATCTACAG | GTAGGCTTTAATGTGTATT |
| 6 7 | 733 | 921 | TTTCAATTGTTTTCCAAAG TTAATGGAGTTTCCTGGACA | TATGATGGAGAAGGGGAAG | GTAAGAGCTATATATGTT |
| 7 8 | 922 | 1023 | GGGTGAATTTTTTATTGTAG ATTTGCAATCTTGTATGATC | TACCAGACATGATCTTTCAG | GTAAAAATCTTTTTTGTCC |
| 8 9 | 1024 | 1164 | TTCCTTTTTTGTTTAATAG GAAAGGTTGTCAATATAGAT | GAAACGTCACTATCAAGAAG | GTAAAGAATTTTGGGGTTGA |
| 9 10 | 1165 | 1312 | TGGGATATTTTCCCCAACAG CTTATCTTAATGGCCATGCA | TCAACCCACTTCCTTCAGAG | GTAATGATAGATTACTGTGT |
| 10 11 | 1313 | 1704 | GTTTGATGTTTGTTTTGCAG AGAACAGAATGGATATAGAC | TCAGTTTTCTCCTGTTGCAG | GTATTTGTGTTGACATTTCC |
| 11 12 | 1705 | 2576 | AAATTTTTTTCAAATTCAG GTGTGCACTCTCCCCATGGCA | AGACAGAGACAAGTGAAGAG | GTAATTTGTTTTCTGTATAT |
| 12 13 | 2577 | 2712 | TTTTAAAAACTTATTTCTGCAG GGATCTGGAGACTTGGATAA | TCAAGGAACTAATTCTCTGG | GTAAGAATGAACTAGGTTTT |

FIGURE 6B: HUMAN AIB1 INTRON/EXON BOUNDARIES

| Exon | cDNA bp 5'exon | cDNA bp 3'exon | 3'intron splice site | Exon sequence (5' to 3') | 5'intron splice site |
|---|---|---|---|---|---|
| 14 | | 2907 | TTGTATTGTGTTTCAACAG | GTTTGAAAAGTTCACAGTCT | |
| 14 | 2908 | | | AAATTATGGCTCAAGTATGG | GTATGTTATTTCTAATTAGT |
| 15 | | 3280 | AGTATGGCTACCTGTTTTAG | GTGGGCCAAACCGAAATGTG | |
| 15 | 3281 | | | TCTCATGGCACTCAAAATAG | GTGGGGTGTTATTTTGTGAC |
| 16 | | 3452 | GATTGCAAGTCTTTTTCTAG | GCCTCTTCTTAGGAATTCCC | |
| 16 | 3453 | | | TTCCTGAACTTGTCAATCAG | GTAGGTTGCATTAACATGGA |
| 17 | | 3746 | TTTTATGTGTGTGTTAAG | GGACAGGCATTAGAGCCCAA | |
| 17 | 3747 | | | AGAGGCTGCAGGGCCAGCAG | GTAACCAGTCATGTGTTCTT |
| 18 | | 3839 | ACCAACTTGTCTCACCTCAG | TTTTTGAATCAGAGCCGACA | |
| 18 | 3840 | | | GGCCTATGATGCAGCCCCAG | GTGAGCTCCCAGGTGAGGAT |
| 19 | | 4134 | CACTCTTTCTTGGGTATTAG | CAGGGTTTTCTTAATGCTCA | |
| 19 | 4135 | | | TCCATATCAACCAAATTATG | GTAAATCTGACAATGAAAAT |
| 20 | | 4309 | TTCTGTTTATTTTGTAAG | GAATGGGACAACAACCAGAT | |
| 20 | 4310 | | | GGAAATTTGGCCAGGAACAG | GTAAAGAACAGTGACTTATA |
| 21 | | 4450 | TACCATTTGTTTACTTACAG | CTCCTTTTCCCAGCAGCAGT | |
| 21 | 4451 | | | TGCCTATGGTCCTGATCAG | GTATGGGATCGATTCCTTAC |
| 22 (18) | | | TTTTTCCTGGTTGCTGACAG | AAATACTGCTGACATCTCTG | |

AIB1, A NOVEL STEROID RECEPTOR CO-ACTIVATOR

PRIORITY CLAIM

This application claims priority under 35 U.S.C. §119 to PCT Application No. PCT/US8912689, filed Jun. 17, 1998, which claims priority to U.S. Provisional Application No. 60/049,728, filed Jun. 17, 1997.

BACKGROUND OF THE INVENTION

Breast cancer arises from estrogen-responsive breast epithelial cells. Estrogen activity is thought to promote the development of breast cancer, and many breast cancers are initially dependent on estrogen at the time of diagnosis. Anti-estrogen compositions have therefore been used to treat breast cancer.

A frequent mechanism of increased gene expression in human cancers is amplification, i.e., the copy number of a DNA sequence is increased, in a cancer cell compared to a non-cancerous cell. In breast cancer, commonly amplified regions are derived from 17q21, 8q24, and 11q13 which encode erbB-2, c-myc, and cyclic D1 respectively (Devilee et al., 1994, Crit. Rev. Oncog. 5:247–270). Recently, molecular cytogenetic studies have revealed the occurrence in breast cancers of additional regions of increased DNA copy number (Isola et al., Am. J. Pathol. 147:905–911, 1995; Kallioniemi et al., Proc. Nati. Acad. Sci. USA 91:2156–2160, 1994; Muleris et al., Genes Chromo. Cancer 10:160–170, 1994; Tanner et al., Cancer Research 54:4257–4260, 1994; Guan et al., Nat. Genet. 8:155–161, 1994).

Breast cancer is the second leading cause of cancer deaths in American women, and it is estimated that an American woman has at least a 10% cumulative lifetime risk of developing this disease. Early diagnosis is an important factor in breast cancer prognosis and affects not only survival rate, but the range of therapeutic options available to the patient. For instance, if diagnosed early, a "lumpectomy" may be performed, whereas later diagnosis tends to be associated with more invasive and traumatic surgical treatments such as radical mastectomy. The treatment of other cancers likewise is benefitted by early diagnosis, for instance the prognosis in the treatment of lung cancer, colorectal cancer and prostate cancers is greatly improved by early diagnosis. There is a need for a simple and reliable method of diagnosis of cancers in general and of breast cancer in particular. There is a need for a method of screening for compounds that inhibit the interaction between an estrogen receptor ER and an ER-dependent nuclear receptor co-activator molecule in order to identify molecules useful in research diagnosis and treatment of cancer. There is also a need for a method for identifying tamoxifen-sensitive cancer patients in order to better manage treatment. A solution to these needs would improve cancer treatment and research and would save lives.

SUMMARY OF THE INVENTION

The inventors have discovered that the AIB1 protein (Amplified In Breast Cancer-1) is a member of the Steroid Receptor Coactivator-1 (SRC-1) family of nuclear receptor co-activators that interacts with estrogen receptors (ER) to enhance ER-dependent transcription. The inventors have further discovered that the AIB1 gene is amplified and over-expressed in certain cancers including breast cancer, and that detection of amplified AIB1 genes can therefore be used to detect cancerous cells. Importantly, the inventors have also found that AIB1 amplification is not confined to breast cancer but is also found in cancers of the lung, ovary, head and neck, colon, testicles, bladder, prostate, endometrium, kidney, stomach and also in pheochromocytoma, melanoma, ductal carcinoma and carcinoid tumor. Such a finding means that AIB1 may be useful in the detection and treatment of all of the aforementioned cancers which include some of the most prevalent and deadly diseases in the western world.

The inventors have also discovered that AIB1 interacts with the proteins p300 and CBP, which are nuclear cofactors that interact with other nuclear factors to promote transcription (Chacravarti et al., Nature (383) 99–103 1996; Lundblad et al., Nature (374) 85–88 1995). The inventors have, furthermore, determined that in cells with stable over-expression of AIB1, there is a dramatic increase in steroid receptor activation (almost a 100-fold increase) leading to a corresponding increase in transcriptional activation. The inventors have also used monoclonal anti-AIB1 antibodies to demonstrate that AIB1 gene amplification is directly correlated with increased AIB1 expression, and that these amplified copies of the gene are expressed in physiological conditions. The inventors have found that AIB1 is the human ortholog of the mouse ER-dependent transcriptional activator p/CIP, with the proteins having an overall amino acid identity of 81.6%. These finding support the physiological role for AIB1 in cancer cells as a cofactor involved in transcriptional regulation.

The invention features a substantially pure DNA which includes a sequence encoding an AIB1 polypeptide, e.g., a human AIB1 polypeptide, or a fragment thereof. The DNA may have the sequence of all or part of the naturally-occurring AIB1-encoding DNA or a degenerate variant thereof. AIB1-encoding DNA may be operably linked to regulatory sequences for expression of the polypeptide. A cell containing AIB1 encoding DNA is also within the invention.

The invention also includes a substantially pure DNA containing a polynucleotides which hybridizes at high stringency to a AIB1-encoding DNA or the complement thereof. A substantially pure DNA containing a nucleotide sequence having at least 50% sequence identity to the full length AIB1 CDNA, e.g., a nucleotide sequence encoding a polypeptide having the biological activity of a AIB1 polypeptide, is also included.

The invention also features a substantially pure human AIB1 polypeptide and variants thereof, e.g., polypeptides with conservative amino acid substitutions or polypeptides with conservative or non-conservative amino acid substitutions which retain the biological activity of naturally-occurring AIB1.

Diagnostic methods, e.g., to idertify cells which harbor an abnormal copy number of the AIB1 DNA, arc also encompassed by the invention. An abnormal copy number, e.g., greater than the normal diploid copy number, of AIB1 DNA is indicative of an aberrantly proliferating cell, e.g., a steroid hormone-responsive cancer cell.

The invention also includes antibodies, e.g., a monoclonal antibody or polyclonal antisera, which bind specifically to AIB1 and can be used to detect the level of expression of AIB1 in a cell or tissue sample. An increase in the level of expression of AIB1 in a patient-derived tissue sample compared to the level in normal control tissue indicates the presence of a cell proliferative disorder such as cancer.

Screening methods to identify compounds which inhibit an interaction of AIB1 with a steroid hormone receptor, thus disrupting a signal transduction pathway which leads to aberrant cell proliferation, is also within the invention. Proliferation of a cancer cell can therefore be reduced by administering to an individual, e.g., a patient diagnosed with a steroid-responsive cancer, a compound which inhibits expression of AIB1.

The invention also includes a knockout mutant, for example a mouse (or other mammal) from which at least one AIB1 gene has been selectively deleted from its genome. Such a mouse is useful in research, for instance, the phenotype gives insight into the physiological role of the deleted gene. For instance the mutant may be defective in specific biochemical pathways; such a knockout mutant may be used in complementation experiments to determine the role of other genes and proteins to determine if any such genes or proteins complement for the deleted gene. Homozygous and heterozygous mutants are included in this aspect of the invention.

The present invention also includes a mutant organism, for example a mammal such as a mouse which contains more than the normal number of AIB1 genes in its genome. Such a mouse may contain additional copies of the AIB1 gene integrated into its chromosomes, for instance in the form of a pro-virus, or may carry additional copies on extra-chromosomal elements such as plasmids. Such a mutant mouse is useful for research purposes, to elucidate the physiological or pathological role of AIB1. For instance, the role of AIB1 expression as cause or effect in cancers may be investigated by including or transplanting tumors into such mutants, and comparing such mutants with normal mice having the same cancer.

The present invention also includes a mutant organism, for example a mammal, e.g. a mouse, that contains, either integrated into a chromosome or on a plasmid, at least one copy of the AIB1 gene driven by a non-native promoter. Such a promoter may be constitutive or may be inducible. For instance, the AIB1 gene may be operatively linked to a mouse mammary tumor virus (MMTV) promoter or other promoter from a mammalian virus allowing manipulation of AIB1 expression. Such a mutant would be useful for research purposes to determine the physiological or pathological role of AIB1. For instance, over or under expression could be affected and physiological effects observed.

The invention also includes methods for treatment of cancers that involve functions of or alterations in the signaling pathways that use p300 and/or CBP as signal transducing molecules. The treatments of the invention involve targeting of the AIB1 protein or AIB1 gene to enhance or reduce interaction with p300 and/or CBP proteins. For instance, the AIB1 gene sequence as disclosed herein may be used to construct an anti-sense nucleotide. An anti-sense RNA may be constructed that is anti-parallel and complementary to the AIB1 transcript (or part thereof) and which will therefore form an RNA-RNA duplex with the AIB1 transcript, preventing transcription and expression of AIB1. Alternatively, treatments may comprise contacting an AIB1 protein with a molecule that specifically binds to the AIB1 molecule in vivo, thereby interfering with AIB1 binding with other factors such as p300 or CBP. Such processes are designed to inhibit signal transduction pathways involving AIB1, p300, CBP and other factors and therefore inhibit cancer cell proliferation that is effected via these pathways. As explained in more detail below, AIB1 overexpression results in increased ER-dependent transcriptional activity which confers a growth advantage upon AIB1 amplification-bearing clones during the development and progression of estrogen-dependent cancers.

Compounds which inhibit or disrupt the interaction of an AIB1 gene product with a steroid hormone receptor, e.g., ER, are useful as anti-neoplastic agents for the treatment of patients suffering from steroid hormone-responsive cancers such as breast cancer, ovarian cancer, prostate cancer, and colon cancer.

AIB1 polypeptides or peptide mimetics of such polypeptides, e.g., those contaig domains which interact with steroid hormone receptors, can be administered to patients to block the interaction of endogenous intracellular AIB1 and a steroid hormone receptor, e.g., ER in an aberrantly proliferating cell. It is likely that AIB1 interacts with a wide range of human transcriptional factors and that regulation of such interactions will have important therapeutic applications.

Other features and advantages of the invention will be apparent from the following description of the preferred embodiments thereof, and from the claims.

SEQUENCE LISTING

The nucleic acid and amino acid sequences listed in the accompanying Sequence Listing are shown using standard letter abbreviations for nucleotide bases and three-letter code for amino acids. Only one strand of each nucleic acid sequence is shown, but the complementary strand is understood to be included by any reference to the displayed strand.

SEQ ID NO:1 shows the nucleic acid sequence of AIB1 cDNA and the corresponding amino acid sequence.

SEQ ID NO:2 shows the amino acid sequence of the Per/Amt/Sim (PAS) domain of AIB1.

SEQ ID NO:3 shows the amino acid sequence of the basic helix-loop-helix domain (bHLH) of AIB1.

SEQ ID NO:4 shows the amino acid sequence of the human AIB1 protein.

SEQ ID NO:5 shows the nucleic acid sequence of primer N8F1.

SEQ ID NO:6 show the nucleic acid sequence of the forward primer designed from the 5' sequence of pCMVSPORT-B11, PM-U2.

SEQ ID NO:7 shows the nucleic acid sequence of the reverse primer designed from the 5' sequence of pCMVSPORT-B11, PM-U2.

SEQ ID NO:8 shows the amino acid sequence of the ER-interacting domain of AIB1.

SEQ ID NO:9 shows the nucleic acid sequence of pCIP, the mouse ortholog of AIB1 and the amino acid sequence for this gene.

SEQ ID NO:10 shows the nucleic acid sequence of the forward primer AIB1/mESTF1 used to screen mouse BAC.

SEQ ID NO:11 shows the nucleic acid sequence of the reverse primer AIB1/mESTF1 used to screen mouse BAC.

SEQ ID NO:12 shows the amino acid sequence of pCIP, the mouse ortholog of AIB1.

BRIEF DESCRIPTION OF THE DRAWINGS

FIG. 5A and FIG. 5B are a table showing the introns and exons of the mouse AIB1 gene (pCIP) (SEQ ID NO:9). The "Exon" column refers to the number of the exon; "cDNA bp 5'-exon" refers to the nucleotide position in the mouse cDNA sequence for the 5' exon; "cDNA bp 3' exon" refers to the last few nucleotides of the 3' position of the intron. "Exon sequence" refers to the exon itself. "5' intron" refers to the adjacent intron reading from the exon into the splice donor elinucleotides (usually GT).

FIG. 6 A and FIG. 6B are a table showing the introns and exons of the human AIB1 gene (SEQ ID NO:1). The "Exon" column refers to the number of the exon; "cDNA bp 5'-exon" refers to the nucleotide position in the mouse cDNA sequence for the 5' exon; "cDNA bp 3' exon" refers to the last few nucleotides of the 3' position of the intron. "Exon sequence" refers to the exon itself. "5' intron" refers to the adjacent intron reading from the exon into the splice donor elinucleotides (usually GT).

DETAILED DESCRIPTION

Figures 1A, 1B:
FIG. 1A is a diagram of an amino acid sequence of full length AIB1 (SEQ ID NO:4) in which residues highlighted in black are identical in AIB1, TIF2, and SRC1. Residues identical with TIF2 (GenBank Accession No. X97674) or SRC-1 (GenBank Accession No. U59302) are highlighted in grey or boxed, respectively.
FIG. 1B is a diagram showing the structural features of AIB1. The following domains are indicated: bHLH domain, PAS domains (with the highly conserved PAS A and B regions shown in dark gray), S/T (serine/threonine)-rich regions, and a group of charged residues (+/−). A glutamine-rich region and polyglutamine tract are also indicated. The numbers beneath the diagram indicate the location (approximate residue number) of the domain with respect to the amino acid sequence shown in FIG. 1A. The alignment was generated using DNASTAR software.

The invention is based on the discovery of a novel gene, amplified in breast cancer-1 (AIB1), which is overexpressed in breast cancer. AIB1 has the structural features of a co-activator of the steroid hormone receptor family. The steroid hormone estrogen and other related steroid hormones act on cells through specific steroid receptors.

Members of the steroid receptor coactivator (SRC) family of transcriptional co-activators interact with nuclear hormone receptors to enhance ligand-dependent transcription. AIB1 is a novel member of the SRC family which was found to be overexpressed in breast cancers. The AIB1 gene is located at human chromosome 20q. High-level AIB1 amplification and overexpression were observed in several estrogen receptor (ER) positive breast and ovarian cancer cell lines, as well as in uncultured breast cancer specimens. AIB1 amplification is not confined to breast cancer but is also found in cancers of the lung, ovary, head and neck, colon, testicles, bladder, prostate, endometrium, kidney, stomach and also in pheochromocytoma, melanoma, ductal carcinoma and carcinoid tumor. Transfection of AIB1 into cells resulted in marked enhancement of estrogen-dependent transcription. These observations indicated that AIB1 functions as a co-activator of steroid hormone receptors such as ER (including estrogen receptor α (ERα) and estrogen receptor β (ERβ)), androgen receptor (e.g., expressed in prostate cells), retinoid receptor (e.g., isoforms α, γ, and retinoid X receptor (RXR)), progesterone receptor (e.g., expressed in breast cells), mineralocorticoid receptor (implicated in salt metabolism disorders), vitamin D receptor (implicated in calcium metabolism disorders), thyroid hormone receptor (e.g, thyroid hormone receptor α), or glucocorticoid receptor (e.g., expressed in spleen and thymus cells). The altered expression of AIB1 contributes to the initiation and progression of steroid hormone-responsive cancers by increasing the transcriptional activity of the steroid receptor.

A substantially pure DNA which includes an AIB1-encoding polynucleotides (or the complement thereof) is claimed. By "substantially pure DNA" is meant DNA that is free of the genes which, in the naturally-occurring genome of the organism from which the DNA of the invention is derived, flank the AIB1 gene. The term therefore includes, for example, a recombinant DNA which is incorporated into a vector, into an autonomously replicating plasmid or virus, or into the genomic DNA of a prokaryote or cukaryote at a site other than its natural site; or which exists as a separate molecule (e.g., a cDNA or a genomic or cDNA fragment produced by PCR or restriction endonuclease digestion) independent of other sequences. It also includes a recombinant DNA which is part of a hybrid gene encoding an additional polypeptide sequence. Preferably, the polypeptide includes a Per/Arnt/Sim (PAS) domain (LLQALDGFLFVVNRDGNIVFVSENVTQYLQYKQE DLVNTSVYNILHEEDRKDFLKNLPKST VNGVSWT-NETQRQKSHTFNCRMLMKTPHDILEDI-NASPEMRQRYETMQCFALSQPRAMME EGEDLQSC-MICVARRITTGERTFPSNPESFITRHDLSGKVVNIDT NSLRSSMRPGFEDIIRRCIQ; SEQ. I.D. NO. 2) and/or a basic helix-loop-helix (bHLH) domain (RKRKLPCDTPGQGLTCSGEKRRREQESKYIEELAE LISANLSDIDNFNVKPD KCAILKETVRQIR-QIKEQGKT; SEQ. I.D. NO. 3); more preferably, the AIB1 polypeptide includes the amino acid sequence of the entire naturally-occurring AIB1 protein (FIG. 1; SEQ. I.D. NO. 4). Preferably, the peptide includes an ER-interacting domain of AIB1 (e.g., a domain comprising approximately amino acids 300 to 1250: CIQRFFSLNDGQSWSQKRHYQEAYLNG-HAETPVYRFSLADGTIVTAQTKSKLF RNPVT-NDRHGFVSTHFLQREQNGYRPNPNPVGQ-GIRPPMAGCNSSVGGMSMS PNQGLQMPSSRAYGLADPSTTGQMS-GARYGGSSNIASLTPGPGMQSPSSYQNNNYGLNMSS PPHGSPGLAPNQQNIMISPRNRGSPKI-ASHQFSPVAGVHSPMASSGNTGNHSFSSSSLSALQAI SEGVGTSLLSTLSSPGPKLDNSPNM-NITQPSKVSNQDSKSPLGFYCDQN-PVESSMCQSNSRDH LSDKESKESSVEGAENQRG-PLESKGHKKLLQLLTCSSDDRGHSSLTNSPLDSSCK ESSVSVTS PSGVSSSTSGGVSSTSNM-HGSLLQEKHRILHKLLQNGNSPAEVAKI-TAEATGKDTSSITSCGD GNVVKQEQLSPKKKEN-NALLRYLLDRDDPSDALSKELQPQVEGVDNKMSQ CTSSTIPSSSQE KDPKIKTETSEEGSGDLDNLDAI-LGDLTSSDFYNNSISSNGSHLGT-KQQVFQGTNSLGLKSSQ SVQSIRPPYNRAVSLD-SPVSVGSSPPVKNISAFPMLPKQPMLGGNPRMMDS QENYGSSMGGP NRNVTVTQTPSSGDWGLPNSK-AGRMEP- MNSNSMGRPGGDYNTSLPRPALGGSIPTLPLRSN SIP-
GARPVLQQQQQMLQMRPGEIPMGMGAN-
PYGQAAASNQLGSWPDGMLSMEQVSHGTQ
NRPLLRNSLDDLVGPPSNLEGQSDER-
ALLDQLHTLLSNTDATGLEEIDRALGIPELVNQGQA
LEPKQDAFQGQEAAVMMDQKAGLYGQ-
TYPAQGPPMQGGFHLQGQSPSFNSMMNQMNQQ
GNFPLQGMHPRANIMRPRTNTPKQLRM-
QLQQRLQGQQFLNQSRQALELKMENPTAGGAA
VMRPMMQPQQGFLNAQMVAQRSRELLSH-
HFRQQRVAMMMQQQQQQQ (SEQ. I.D. NO. 8). A cell containing substantially purified AIB1-encoding DNA is also within the invention.

The invention also includes a substantially pure DNA which contains a polynucleotide which hybridizes at high stringency to an AIB1 cDNA having the sequence of SEQ. I.D. NO. 1, or the complement thereof and a substantially pure DNA which contains a nucleotide sequence having at least 50% (for example at least 75%, 90%, 95%, or 98–100%) sequence identity to SEQ. I.D. NO. 1, provided the nucleotide sequence encodes a polypeptide having the biological activity of a AIB1 polypeptide. By "biological activity" is meant steroid receptor co-activator activity. For example, allelic variations of the naturally-occurring AIB1-encoding sequence (SEQ. I.D. NO. 1) are encompassed by the invention. Sequence identity can be determined by comparing the nucleotide sequences of two nucleic acids using the BLAST sequence analysis software, for instance, the NCBI gapped BLAST 2.0 program set to default parameters. This software is available from The National Center for Biotechnology Information (www.ncbi.nlm,nih.gov/BLAST).

Hybridization is carried out using standard techniques such as those described in Ausubel et al., *Current Protocols in Molecular Biology*, John Wiley & Sons, (1989). "High stringency" refers to DNA hybridization and wash conditions characterized by high temperature and low salt concentration, e.g., wash conditions of 65° C. at a salt concentration of approximately 0.1×SSC. "Low" to "moderate" stringency refers to DNA hybridization and wash conditions characterized by low temperature and high salt concentration, e.g. wash conditions of less than 60° C. at a salt concentration of at least 1.0×SSC. For example, high stringency conditions may include hybridization at about 42° C., and about 50% formamide; a first wash at about 65° C., about 2×SSC, and 1% SDS; followed by a second wash at about 65° C. and about 0.1%×SSC. Lower stringency conditions suitable for detecting DNA sequences having about 50% sequence identity to an AIB1 gene are detected by, for example, hybridization at about 42° C. in the absence of formamide; a first wash at about 42° C., about 6×SSC, and about 1% SDS; and a second wash at about 50° C., about 6×SSC, and about 1% SDS.

A substantially pure DNA including (a) the sequence of SEQ ID NO. 1 or (b) a degenerate variant thereof is also within the invention. The AIB1-encoding DNA is preferably operably linked to regulatory sequences (including, e.g., a promoter) for expression of the polypeptide.

By "operably linked" is meant that a coding sequence and a regulatory sequence(s) are connected in such a way as to permit gene expression when the appropriate molecules (e.g., transcriptional activator proteins) are bound to the regulatory sequence(s).

The invention also includes a substantially pure human AIB1 polypeptide or fragment thereof. The AIB1 fragment may include an ER-interaction domain such as one having the amino acid sequence of SEQ. I.D. NO. 8. Alternatively, the fragment may contain the amino acid sequence of SEQ. I.D. NOS. 2, 3, or 4.

Screening methods to identify candidate compounds which inhibit estrogen-dependent transcription, AIB1 expression, or an AIB1/ER interaction (and as a result, proliferation of steroid hormone-responsive cancer cells) are within the scope of the invention. For example, a method of identifying a candidate compound which inhibits ER-dependent transcription is carried out by contacting the compound with an AIB1 polypeptide and determining whether the compound binds to the polypeptide. Binding of the compound to the polypeptide indicates that the compound inhibits ER-dependent transcription, and in turn, proliferation of steroid hormone-responsive cancer cells. Preferably, the AIB1 polypeptide contains a PAS domain or a bHLH domain. Alternatively, the method is carried out by contacting the compound with an AIB1 polypeptide and an ER polypeptide and determining the ability of the compound to interfere with the binding of the ER polypeptide with the AIB1 polypeptide. A compound which interferes with an AIB1/ER interaction inhibits ER-dependent transcription.

A method of screening a candidate compound which inhibits an interaction of an AIB1 polypeptide with an ER polypeptide in a cell includes the steps of (a) providing a GAL4 binding site linked to a reporter gene; (b) providing a GAL4 binding domain linked to either (i) an AIB1 polypeptide or (ii) an ER polypeptide; (c) providing a GAL4 transactivation domain II linked to the ER polypeptide if the GAL4 binding domain is linked to the AIB1 polypeptide or linked to the AIB1 polypeptide if the GAL4 binding domain is linked to the ER polypeptide; (d) contacting the cell with the compound; and (e) monitoring expression of the reporter gene. A decrease in expression in the presence of the compound compared to that in the absence of the compound indicates that the compound inhibits an interaction of an AIB1 polypeptide with the ER polypeptide.

Diagnostic methods to identify an aberrantly proliferating cell, e.g., a steroid hormone-responsive cancer cell such as a breast cancer cell, ovarian cancer cell, or prostate cancer cell, are also included in the invention. For example, a method of detecting an aberrantly proliferating cell in a tissue sample is carried out by determining the level of AIB1 gene expression in the sample. An increase in the level of gene expression compared to that in a normal control tissue indicates the presence of an aberrantly proliferating cell. AIB1 gene expression is measured using an AIB1 gene-specific polynucleotides probe, e.g. in a Northern assay or polymerase chain reaction (PCR)-based assay, to detect AIB1 mRNA transcripts. AIB1 gene expression can also be measured using an antibody specific for an AIB1 gene product, e.g., by immunohistochemistry or Western blotting.

Aberrantly proliferating cells, e.g., cancer cells, in a tissue sample may be detected by determining the number of cellular copies of an AIB1 gene in the tissue. An increase in the number of gene copies in a cell of a patient-derived tissue, compared to that in normal control tissue indicates the presence of a cancer. A copy number greater than 2 (the normal diploid copy number) is indicative of an aberrantly proliferative cell. Preferably, the copy number is greater than 5 copies per diploid genome, more preferably 10 copies, more preferably greater than 20, and most preferably greater than 25 copies. An increase in copy number compared to the normal diploid copy number indicates that the tissue sample contains aberrantly proliferating steroid hormone-responsive cancer cells. AIB1 copy number is measured by fluorescent in situ hybridization (FISH), Southern hybridization techniques, and other methods well known in the art (Kallioniemi et al., *PNAS* 91: 2156–2160 (1994); Guan et al., *Nature Genetics* 8: 155–161 (1994); Tanner et al., *Clin. Cancer res.* 1: 1455–1461 (1995); Guan et al., *Cancer Res.* 56: 3446–3450 (August 1996); Anzick et al., *Science* 277: 965–968 (August 1997)).

Aberrantly proliferating cells can also be identified by genetic polymorphisms in the polyglutamine tract of AIB1, e.g., variations in the size of this domain which alter AIB1 co-ctivator activity.

The invention also includes methods of treating a mammal, e.g., a human patient. For example, a method of reducing proliferation of a steroid hormone-responsive cancer cell, e.g., an estrogen-responsive breast cancer cell, in a mammal is carried out by administering to the mammal a compound which inhibits expression of AIB1. The compound reduces transcription of AIB1-encoding DNA in the cell. Alternatively, the compound reduces translation of an AIB1 mRNA into an AIB1 gene product in the cell. For example, translation of AIB1 mRNA into an AIB1 gene product is inhibited by contacting the mRNA with antisense polynucleotides complementary to the AIB1 mRNA.

A method of inhibiting ER-dependent transcription in a breast cell of a mammal is carried out by administering an effective amount of an AIB1 polypeptide or a peptide mimetic thereof to the mammal. Preferably, the polypeptide inhibits an AIB1/ER interaction; more preferably, the polypeptide contains an ER-interacting domain; a PAS domain or a bHLH domain of AIB1. By binding to ER, such a polypeptide inhibits binding of AIB1 to ER, thereby inhibiting ER-dependent transcription.

The invention also includes antibodies, e.g., a monoclonal antibody or polyclonal antisera, which bind specifically to AIB1. The term "antibody" as used in this invention includes whole antibodies as well as fragments thereof, such as Fab, Fab', F(ab')$_2$, and Fv which bind to an AIB1 epitope. These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; F(ab')$_2$, a dimer of two Fab' fragments held-together by two disulfide bonds; (4) Fv, a genetically engineered fragment containing the variable region of the light chain and the variable region of the heavy chain expressed as two chains; and (5) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Also within the invention is a method of identifying a tamoxifen-sensitive patient (one who is likely to respond to tamoxifen treatment by a reduction in rate of tumor growth) wherein the method includes the steps of (a) contacting a patient-derived tissue sample with tamoxifen; and (b) determining the level of AIB1 gene expression or amplification in the sample. An increase in the level of expression or gene copy number compared to the level or cellular copy number in normal control tissue indicates that the patient is tamoxifen-sensitive.

AIB1 gene expression is measured using an AIB1 gene-specific polynucleotide probe, e.g., in a Northern blot or PCR-based assay to detect AIB1 mRNA transcripts or in a Southern blot or FISH assay to detect amplification of the gene (which correlates directly with AIB1 gene expression). Alternatively, AIB1 gene expression is measured by detecting an AIB1 gene product, e.g., using an AIB1-specific antibody.

Transgenic mammals, e.g., mice, which overexpress an AIB1 gene product, e.g., by virtue of harboring multiple copies of AIB1-encoding DNA, are also within the invention.

"Transgenic" as used herein means a mammal which bears a transgene, a DNA sequence which is inserted by artifice into an embryo, and which then becomes part of the genome of the mammal that develops from that embryo. Any non-human mammal which may be produced by transgenic technology is included in the invention; preferred mammals include, mice, rats, cows, pigs, sheep, goats, rabbits, guinea pigs, hamsters, and horses.

By "transgene" is meant DNA which is partly or entirely heterologous (i.e., foreign) to the transgenic mammal, or DNA homologous to an endogenous gene of the transgenic mammal, but which is inserted into the mammal's genome at a location which differs from that of the natural gene.

Also within the invention is a knockout mutant, for instance a knockout mouse wherein the mouse has had at least one copy of the AIB1 gene (also called the pCIP gene in mice) deleted from its genome. Such a knockout mutant would be useful in research, for instance the phenotype gives insight into the physiological role of AIB1. Complementation experiments using such a knockout mutant can be used to identify other genes and proteins that make up for the lack of AIB1 in the mutant to restore wild-type phenotype.

Also within the invention is a mutant, such as a mouse, which contains more than the normal number of copies of the AIB1 (pCIP) gene, either integrated into a chromosome, for instance as a pro-virus, or in an extra-chromosomal element, such as on a plasmid. Also within the invention is a mutant, for example, a mouse, which contains the AIB1 (pCIP) gene driven by a non-native promoter, such as a constitutive or an inducible promoter, such as the mouse mammary tumor virus (MMTV) promoter.

The invention also includes methods of treatment for cancers the growth of which involves alternations of signaling pathways involving p300 and/or CBP. For example, AIB1 (pCIP) may be contacted with a molecule that binds to AIB1 and inhibits AIB1's interaction with p300, thereby disrupting signaling of this pathway and reducing transcription of molecules whose transcription is positively regulated by this pathway; thereby reducing tumor growth.

EXAMPLE 1

Cloning and Expression of AIB1

A. Cloning of AIB1

Chromosome microdissection and hybrid selection techniques were used to isolate probes and clone gene sequences which map to chromosome 20q, one of the recurrent sites of DNA amplification in breast cancer cells identified by molecular cytogenetics (Kallioniemi et al., *PNAS* 91: 2156–2160 (1994); Guan et al., *Nature Genetics* 8: 155–161 (1994); Tanner et al., *Clin. Cancer Res.* 1: 1455–1461 (1995); Guan et al., *Cancer Res.* 56: 3446–3450 (August 1996); Anzick et al., *Science* 277: 965–968 (August 1997)). AIB1 is a member of the SRC-1 family of nuclear receptor (NR) co-activators. AIB1 functions to enhance ER-dependent transcription. SRC-1 and the closely related TIF2 are steroid receptor co-activators with an affinity for NRs. The mouse ortholog of human AIB1 is called pCIP. In this application pCIP and AIB1 will be used synonymously unless the contrary is clearly expressed.

To characterize AIB1, the full length cDNA was cloned and sequenced. An AIB1 specific primer N8F1 (5'-TCATCACTTCCGACAACAGAGG-3'; SEQ. I.D. NO. 5) was biotinylated and used to capture cDNA clones from a human lung cDNA library (Gibco, BRL) using the GEN-ETRAPPER cDNA Positive Selection System (Gibco, BRL). The largest clone (5.8 kb), designated pCMVSPORT-B11, was selected for sequence analysis. To obtain full-length AIB1-encoding DNA, a random-primed library from BT-474 was constructed in bacteriophage λ-Zap (Stratagene) and hybridized with a 372 bp $^{32}$P-labeled PCR product amplified from a human spleen cDNA library using primers designed form the 5' sequence of pCMVSPORT-B11, PM-U2 (5'-CCAGAAACGTCACTATCAAG-3', forward primer; SEQ. I.D. NO. 6) and B11-11RA (5'-TTACTGGAACCCCCATACC-3', reverse primer; SEQ. I.D. NO. 7). Plasmid rescue of 19 positive clones yielded a clone, pBluescript-R22, which overlapped pCMVSPORT-B11 and contained the 5' end of the coding region. To generate a full length AIB1 clone, the 4.85 kb HindIII/XhoI fragment of pCMVSPORT-B11 was subcloned into HindIII/XhoI sites of pBluescript-R22. The 4.84 kb NotI/NheI fragment of the full length clone containing the entire coding region was then subcloned into the NotI/XbaI sites of the expression vector, pcDNA3.1 (Invitrogen), generating pcDNA3.1-AIB1.

The cloned DNA sequence (SEQ. I.D. No. 1) revealed an open reading frame (beginning at the underlined "ATG") encoding a protein of 1420 amino acids with a predicted molecular weight of 155 kDa (FIG. 1A). Database searches with BLASTP identified a similarity of AIB1 with TIF2 (45% protein identity) and SRC-1 (33% protein identity). Like TIF2 and SRC-1, AIB1 contains a bHLH domain preceding a PAS domain, serine/threonine-rich regions, and a charged cluster (FIG. 1B). There is also a glutamine-rich region which, unlike SRC-1 and TIF2, contains a polyglutamine tract (FIG. 1B). The polyglutamine tract of AIB1 is subject to genetic polymorphism. Variations in the size of this domain alter AIB1 co-activator activity.

B. Expression of AIB1

Amplification and expression of AIB1 in several ER positive and negative breast and ovarian cancer cell lines was examined. Established breast cancer cell lines used in the experiments described below (see, e.g., FIG. 2) were obtained from the American Type Culture Collection (ATCC): BT-474, MCF-7, T-47D, MDA-MB-361, MDA-MB-468, BT-20, MDA-MB436, and MDA-MB-453; the Arizona Cancer Center (ACC): UACC-812; or the National Cancer Institute (NCI): ZR75-1.

AIB1 gene copy number was determined by FISH. For FISH analysis, interphase nuclei were fixed in methanol:acetic acid (3:1) and dropped onto microscope slides. AIB1 amplification was detected in the breast cancer cell line ZR75-1, the ovarian cancer cell line BG-1, and two uncultured breast cancer samples. Intra-chromosomal amplification of AIB1 was apparent in metaphase chromosomes of ZR75-1 and BG1. Numerous copies of AIB1 were resolved in the adjacent interphase nuclei. Extrachromosomal copies (e.g., in episomes or double minute chromosomes) of AIB1 have also been detected. The Spectrum-Orange (Vysis) labeled AIB1 P1 probe was hybridized with a biotinylated reference probe for 20q11 (RMC20P037) or a fluorescein labeled probe for 20p (RMC20C039).

Figure 2:
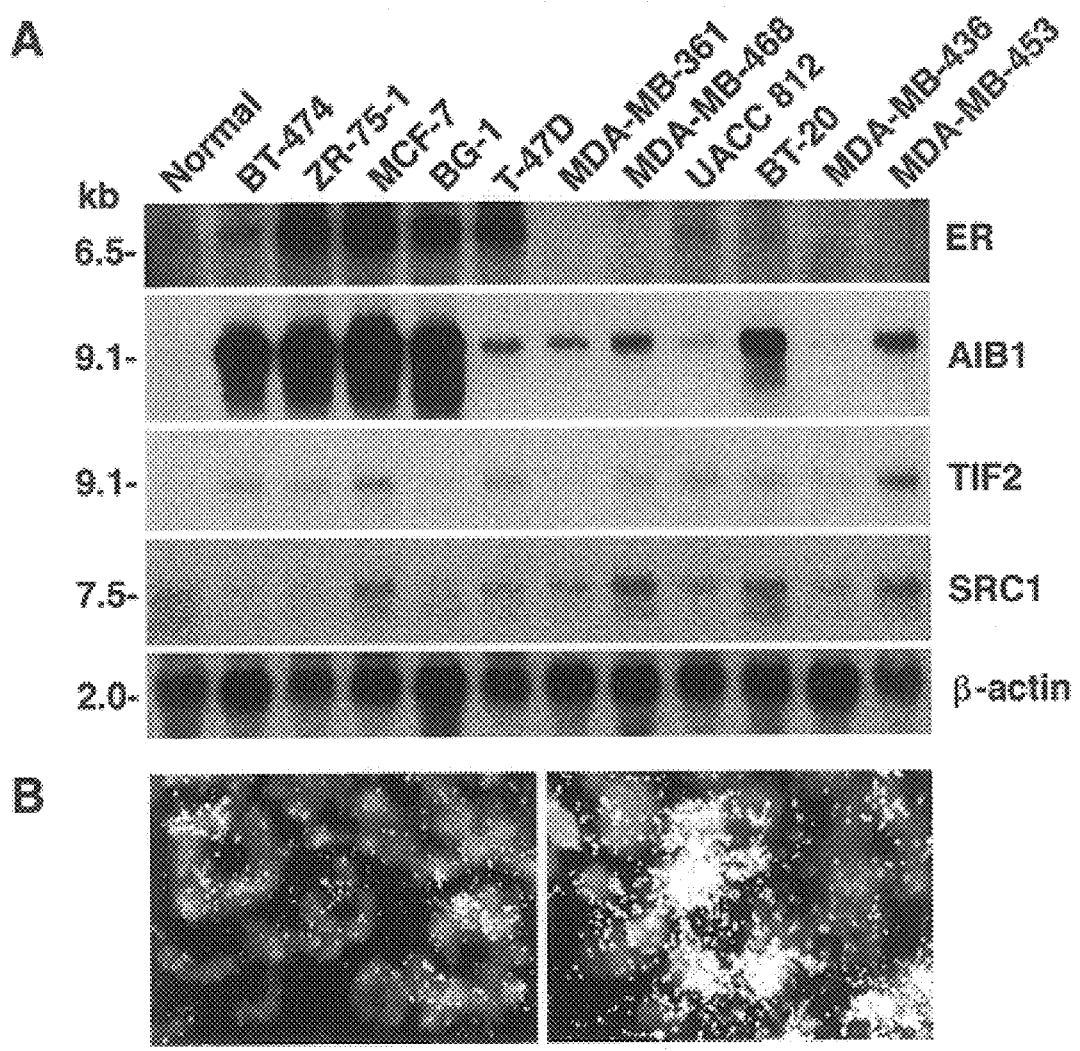
FIGS. 2A and 2B are a photograph of a Northern blot analysis showing increased expression of AIB1 in the cell lines BT-474, ZR-75-1, MCF7, and BG-1.

High level amplification of AIB1 (greater than 20 fold), similar to that observed in BT-474 and MCF-7, was seen in two additional ER-positive cell lines, breast carcinoma ZR75-1, and ovarian carcinoma BG-1 (see FIG. 2). Interphase FISH studies demonstrated that amplification of chromosome 20q in breast cancer is complex, involving several distinct variably co-amplified chromosomal segments derived from 20q11, 20q12, and 20q13. Probes for the 20q11 and 20q13 regions of amplification did not detect amplification in ZR75-1 and BG-1, suggesting that amplification of AIB1 (which maps to 20q12) occurred independently in these cell lines.

To determine if AIB1 amplification also occurred in uncultured cells from patient biopsies, breast cancer specimens were screened for AIB1 amplification by interphase FISH. In two of 16 specimens analyzed, high AIB1 copy number (up to 25 copies/cell) was detected. Both tumor specimens tested came from post-menopausal patients and were ER/PR positive. One of the specimens was obtained from a metastatic tumor of a patient who subsequently responded favorably to tamoxifen treatment.

AIB1 expression was also examined in cells with and without AIB1 amplification and compared to expression of ER, SRC-1 and TIF2 by Northern blotting. In accordance with its amplification status, AIB1 was highly overexpressed in BT-474, MCF-7, ZR75-1, and BG-1 (FIG. 2). Three of the four cell lines exhibiting AIB1 overexpression also demonstrated prominent ER expression, while two others displayed lower but detectable ER expression (BT-474 and BT-20). FIG. 2 also shows that the expression of TIF2 and SRC-1 remained relatively constant in all cell lines tested. Taken together, these observations demonstrate that AIB1 amplification is associated with significant overexpression of AIB1 gene product. The correlation of elevated AIB1 expression with ER positivity in tumors indicates that AIB1 is a component of the estrogen signaling pathway, the amplification of which is selected during cancer development and progression.

Figure 3:
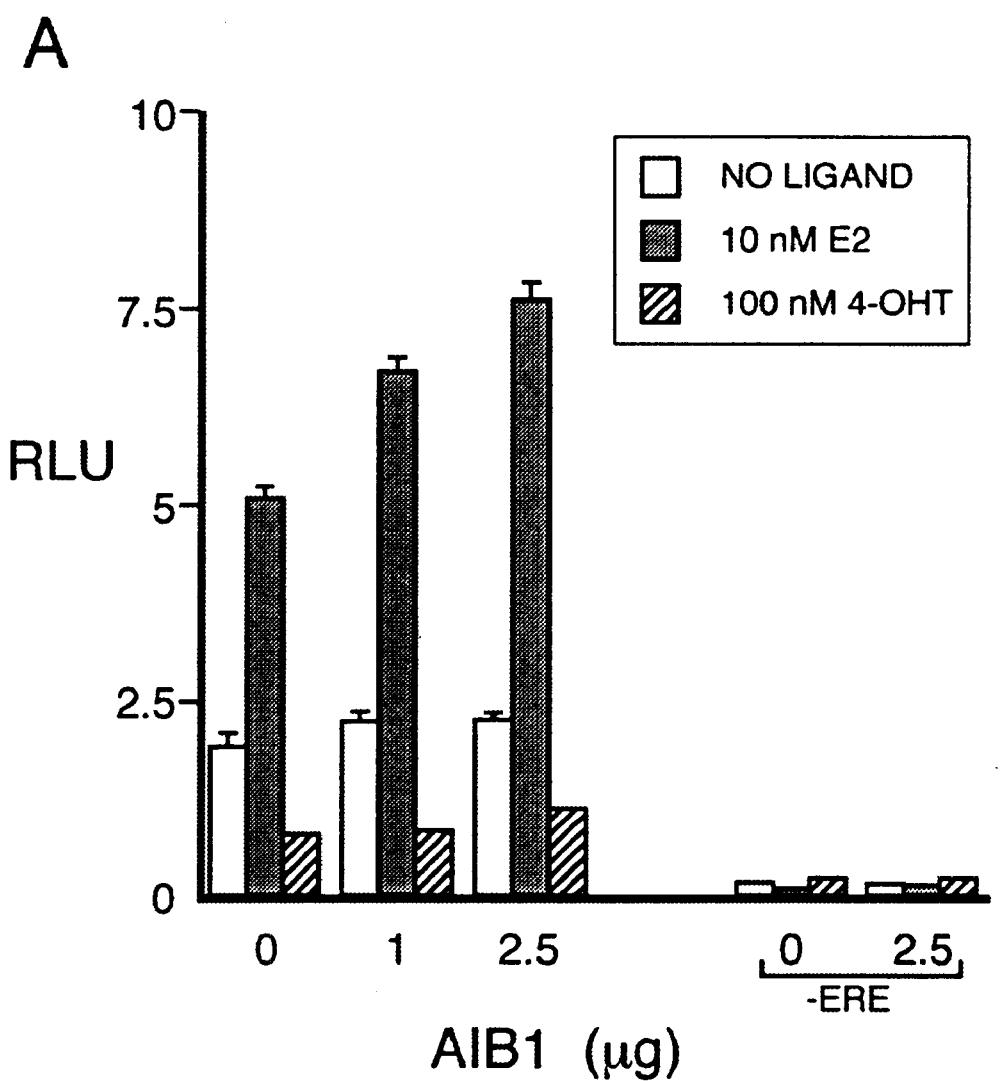
FIG. 3 is a bar graph showing that the addition of full length AIB1 DNA to a cell resulted in an increase of estrogen-dependent transcription from an ER reporter plasmid. COS-1 cells were transiently transfected with 250 ng ER expression vector (pHEGO-hyg), 10 ng of luciferase reporter plasmid (pGL3.luc.3ERE or 10 ng pGL3 lacking ERE) and increasing amounts of pcDNA3.1-AIB1 and incubated in the absence (open bars) or presence of 10 nM 17 β-stradiol (E2, solid bars) or 100 nM 4-hydroxytamoxifen (hatched bars). Luciferase activity was expressed in relative luminescence units (RLU). The data are the mean of three determinations from one of four replicate experiments. Error bars indicate one standard deviation.

To determine whether expression of AIB1 increases ER ligand-dependent transactivation, transient transfection assays were performed. The effect of increasing levels of AIB1 on transcription of an ER dependent reporter was measured. The results demonstrated that co-transfection of AIB1 led to a dose dependent increase in estrogen-dependent transcription (FIG. 3). This effect was not observed when the estrogen antagonist, 4-hydroxytamoxifen (4-OHT), was substituted for 17β-estradiol or when the estrogen response element (ERE) was removed from the reporter plasmid (FIG. 3). A modest increase in basal transcription levels was observed with higher concentrations of AIB1 even in the absence of an ERE suggesting that AIB1 may have an intrinsic transactivation function. These results demonstrate that, like the closely related TIF2 and SRC-1, AIB1 functions as an ER co-activator.

EXAMPLE 2

Characterization of AIB1

A. Functional Domains of AIB1

TIF-2, SRC-1, and AIB1 are characterized by highly conserved N-terminal bHLH and PAS domains. The PAS region functions as a protein dimerization interface in the mammalian aryl hydrocarbon receptor and the aryl hydrocarbon receptor nuclear transporter proteins, as well as the Drosophila transcription factors sim and per. The PAS region (SEQ. I.D. NO. 2) of AIB1 functions as a protein interaction domain, mediating binding between AIB1 and other proteins. However, steroid hormone activators lacking the PAS domain are capable of interacting with nuclear steroid hormone receptors. The highly conserved bHLH domain (SEQ. I.D. NO. 3) participates in protein interactions which mediate or modulate transmission of the hormone signal to the transcriptional apparatus. The ER-interacting domain (SEQ. I.D. NO. 8) mediates binding of AIB1 with a steroid hormone receptor protein.

AIB1 also interacts with the transcriptional integrators CREB binding protein (CBP) and p300. These transcriptional integrators interact directly with the basal transcriptional machinery. The CBP/p300 receptor association domain of AIB1 does not encompass the bHLH/PAS regions.

B. Purification of Gene Products

DNA containing a sequence that encodes part or all of the amino acid sequence of AIB1 can be subcloned into an expression vector, using a variety of methods known in the art. The recombinant protein can then be purified using standard methods. For example, a recombinant polypeptide can be expressed as a fusion protein in procaryotic cells such as *E. coli*. Using the maltose binding protein fusion and purification system (New England Biolabs), the cloned human cDNA sequence is inserted downstream and in frame of the gene encoding maltose binding protein (malE). The malE fusion protein is overexpressed in *E. coli* and can be readily purified in quantity. In the absence of convenient restriction sites in the human cDNA sequence, PCR can be used to introduce restriction sites compatible with the pMalE vector at the 5' and 3' end of the cDNA fragment to facilitate insertion of the cDNA fragment into the vector. Following expression of the fusion protein, it can be purified by affinity chromatography. For example, the fusion protein can be purified by virtue of the ability of the maltose binding protein portion of the fusion protein to bind to amylase immobilized on a column.

To facilitate protein purification, the pMalE plasmid contains a factor Xa cleavage site upstream of the site into which the cDNA is inserted into the vector. Thus, the fusion protein purified as described above can be cleaved with factor Xa to separate the maltose binding protein portion of the fusion protein from recombinant human cDNA gene product. The cleavage products an be subjected to further chromatography to purify recombinant polypeptide from the maltose binding protein. Alternatively, an antibody specific for the desired recombinant gene product can be used to purify the fusion protein and/or the gene product cleaved from the fusion protein. Many comparable commercially available fusion protein expression systems can be utilized similarly.

AIB1 polypeptides can also be expressed in eucaryotic cells, e.g., yeast cells, either alone or as a fusion protein. For example, a fusion protein containing the GAL4 DNA-binding domain or activation domain fused to a functional domain of AIB1, e.g., the PAS domain, the bHLH domain, or the ER-interacting domain, can be expressed in yeast cells using standard methods such as the yeast two hybrid system described below. Alternatively, AIB1 polypeptides can be expressed in COS-1 cells using methods well known in the art, e.g., by transfecting a DNA encoding an AIB1 polypeptide into COS-1 cells using, e.g., the Lipofectamine transfection protocol described below, and culturing the cells under conditions suitable for protein expression.

EXAMPLE 3

Detection of AIB1

A. Detection of Nucleotides Encoding AIB1

Determination of gene copy number in cells of a patient-derived sample is known in the art. For example, AIB1 amplification in cancer-derived cell lines as well as uncultured breast cancer cells was carried out using bicolor FISH analysis as follows. A genomic P1 clone containing AIB1 was labeled with Spectrum Orange-dUTP (Vysis) using the BioPrime DNA Labeling System (Gibco BRL). A 20q11 P1 clone was labeled with Biotin-16-dUTP (BMB) using nick translation. Fluorescent images were captured using a Zeiss axiophot microscope equipped with a CCD camera and IP Lab Spectrum software (Signal Analytics). Interphase FISH analysis of uncultured breast cancer samples was performed using known methods (Kallioniemi et al., *PNAS* 91: 2156–2160 (1994); Guan et al., *Nature Genetics* 8: 155–161 (1994); Tanner et al., *Clin. Cancer res.* 1: 1455–1461 (1995); Guan et al., *Cancer Res.* 56: 3446–3450 (August 1996); Anzick et al., *Science* 277: 965–968 (August 1997)). Alternatively, standard Southern hybridization techniques can be employed to evaluate gene amplification. For example, Southern analysis is carried out using a non-repetitive fragment of genomic AIB1 DNA, e.g., derived from the 20q11 P1 clone described above or another AIB1 gene-containing genomic clone, as a probe.

The level of gene expression may be measured using methods known in the art, e.g., in situ hybridization, Northern blot analysis, or Western blot analysis using AIB1-specific monoclonal or polyclonal antibodies. AIB1 gene transcription was measured using Northern analysis. For example, the data shown in FIG. 2 was obtained as follows. The blot was hybridized sequentially with a probe (ER, AIB1, TIF2, SRC-1, or β-actin as indicated to the left of the photograph). AIB1 expression was compared to that of ER, TIF2, and SRC-1. cDNA clones were obtained from Research Genetics [TIF2 (clone 132364, GenBank accession no. R25318); SRC-1 (clone 418064, GenBank accession no. W90426)], the American Type Culture Collection (pHEGO-hyg, ATCC number 79995), or Clontech (β actin). The AIB1 probe was a 2.2 kb NotI/SacI fragment of pCMVSPORT-B11. The β-actin probe was used as a control for loading error. To avoid cross-hybridization between these related genes and to match signal intensities, similar sized probes from the 3'UTRs of AIB1, TIF2, and SRC-1 were utilized. Each of these probes detected a signal in normal mammary RNA on longer exposure. Electrophoresis, transfer and hybridization of 15 μg total RNA was performed by standard methods.

B. Detection of AIB1 Gene Products

AIB1 polypeptides to be used as antigens to raise AIB1-specific antibodies can be generated by methods known in the art, e.g., proteolytic cleavage, de novo synthesis, or expression of a recombinant polypeptide from the cloned AIB1 gene or a fragment thereof. AIB1-specific antibodies are then produced using standard methodologies for raising polyclonal antisera and making monoclonal antibody-producing hybridoma cell lines (see Coligan et al., eds., Current Protocols in Immunology, 1992, Greene Publishing Associates and Wiley-Interscience). To generate monoclonal antibodies, a mouse is immunized with an AIB1 polypeptide, antibody-secreting B cells isolated from the mouse, and the B cells immortalized with a non-secretory myeloma cell fusion partner. Hybridomas are then screened for production of an AIB1-specific antibody and cloned to obtain a homogenous cell population which produces a monoclonal antibody.

For administration to human patients, antibodies, e.g., AIB1 specific monoclonal antibodies, can be humanized by methods known in the art. Antibodies with a desired binding specificity can be commercially humanized (Scotgene, Scotland; Oxford Molecular, Palo Alto, Calif.).

EXAMPLE 4

Detection of AIB1-related Cell Proliferative Disorders

A. Diagnostic and Prognostic Methods

The invention includes a method of detecting an aberrantly proliferating cell, e.g., a steroid hormone-responsive cancer cell such as a breast cancer cell, an ovarian cancer cell, colon cancer cell, or prostate cancer cell, by detecting the number of AIB1 gene copies in the cell and/or the level of expression of the AIB1 gene product. AIB1 gene amplification or gene expression in a patient-derived tissue sample is measured as described above and compared to the level of amplification or gene expression in normal non-cancerous cells. An increase in the level of amplification or gene expression detected in the patient-derived biopsy sample compared to the normal control is diagnostic of a diseased state, i.e., the presence of a steroid hormone responsive cancer.

Because of the importance of estrogen exposure to mammary carcinogenesis and of anti-strogen treatment in breast cancer therapy, such assays are also useful to determine the frequency of alterations of AIB1 expression in pre-malignant breast lesions (e.g. ductal carcinoma in sits) and during the progression from hormone dependent to hormone independent tumor growth.

The diagnostic methods of the invention are useful to determine the prognosis of a patient and estrogen responsive status of a steroid hormone-responsive cancer.

AIB1 expression can also be measured at the protein level by detecting an AIB1 gene products with an AIB1-specific monoclonal or polygonal antibody preparation.

B. Diagnosis of Tamoxifen-Sensitivity

Overexpression of AIB1, e.g., as a result of AIB1 gene amplification, in steroid hormone-responsive cancers can predict whether the cancer is treatable with anti-endocrine compositions, e.g., tamoxifen. AIB1 amplification or overexpression in a patient-derived tissue sample compared to a normal (non-cancerous) tissue indicates tumor progression.

Absence of AIB1, e.g., loss of all or part of the AIB1 gene, but retention of ER-positivity in steroid hormone-responsive cancers predicts failure or poor responsiveness to anti-endocrine therapy, e.g., administration of anti-estrogen compositions such as tamoxifen. Since loss of AIB1 expression in a cancer cell may indicate a disruption of the ER signal transduction pathway, anti-estrogen therapy may be ineffective to treat such cancers. Patients identified in this manner (who would otherwise be treated with anti-estrogens) would be treated with alternative therapies.

Loss of estrogen receptor in recurrent breast caner is also associated with poor response to endocrine therapy. Up to 30% to 40% of metastases from hormone receptor-positive primary breast cancer do not respond to endocrine therapy. The frequency of hormone receptor status changes between primary and recurrent tumors and whether such a change might explain unresponsiveness to endocrine therapy was examined. Primary breast cancer samples and matched asynchronous recurrences were studied from 50 patients who had not received any adjuvant therapy. ER and progesterone receptor (PR) status was determined immunohistochemically from histologically representative formalin-fixed paraffin-embedded tumor samples. ER status was ascertained by mRNA in situ hybridization. Thirty-five (70%) of 50 primary tumors were positive for ER and 30 (60%) for PR. Hormone receptor status of the recurrent tumor differed from that of the primary tumor in 18 cases (36%). Discordant cases were due to the loss of ER (n=6), loss of PR (n=6), or loss of both receptors (n=6). Receptor-negative primary tumors were always accompanied by receptor-negative recurrences. Among 27 patients with ER-positive primary tumors, loss of ER was a significant predictor (P=0.0085) of poor response to subsequent endocrine therapy. Only one of eight patients (12.5%) with lost ER expression responded to tamoxifen therapy, whereas the response rate was 74% (14 of 19) for patients whose recurrent tumors retained ER expression. Loss of ER expression in recurrent breast cancer predicts poor response to endocrine therapy in primarily ER-positive patients. Evaluation of ER expression and/or AIB1 expression (or gene copy number) is useful to determine the most effective approach to treatment of steroid-responsive cancers.

EXAMPLE 5

Screening of Candidate Compounds

A. In Vitro Assays

The invention includes methods of screening to identify compounds which inhibit the interaction of AIB1 with ER, thereby decreasing estrogen dependent transcription which leads to aberrant cell proliferation. A transcription assay is carried out in the presence and absence of the candidate compound. A decrease in transcription in the presence of the compound compared to that in its absence indicates that the compound blocks an AIB1/ER interaction and inhibits estrogen dependent transcription.

To determine the effect of AIB1 on estrogen-dependent transcription, an ER reporter plasmid can be used. The transcription assays described herein were conducted as follows. COS-1 cells were grown and maintained in phenol-red free DMEM medium supplemented with 10% charcoal-stripped fetal bovine serum. Cells were plated into 6-well culture dishes at $1.5 \times 10^5$ cells/well and allowed to grow overnight. Transfection of cells with the ER reporter plasmid was performed with Lipofectamine (Gibco, BRL) following the manufacturer's protocol. Three ng pRL-CMV were used as an internal control for transfection efficiency. Ligand or ethanol vehicle was added 234 hours post-transfection and cell lysates were harvested 48 hours post-transfection. Reporter activities were determined using the Dual-Luciferase Reporter Assay System (Promega) and the results expressed in relative luminescence units (RLU; luciferase/Renilla luciferase). pRL-CMV and pGL3-promoter were obtained from Promega. pHEGO-hyg was obtained from ATCC. The ER reporter pGL3.luc.3ERE contains three tandem copies of the ERE upstream from the SV40 promoter driving the luciferase gene. Standard mammalian expression vectors were utilized. Empty pcDNA3 vector was added to each of the pcDNA3.1-AIB1 dilutions to maintain constant amounts of plasmid DNA.

Compounds which inhibit the interaction of AIB1 with ER are also identified using a standard co-precipitation assay. AIB1/ER co-precipitation assays are carried out as follows. An AIB1 polypeptide and an ER polypeptide are incubated together to allow complex formation. One of the polypeptides is typically a fusion protein, e.g., GST-AIB1, and the other is tagged with a detectable label, e.g., $^{32}$P-labeled ER). After incubation, the complex is precipitated, e.g., using glutathione-Sepharose beads. The beads are washed, filtered through a glass fiber filter, and collected. The amount of co-precipitated $^{32}$P-label is measured. A reduction in the amount of co-precipitated label in the presence of a candidate compound compared to that in the absence of the candidate compound indicates that the compound inhibits an AIB1/ER interaction Alternatively, a standard in vitro binding assay can be used. For example, one polypeptide, e.g., AIB1, can be bound to a solid support and contacted with the second polypeptide, e.g., ER. The amount of the second polypeptide which is retained on the solid support is then measured. A reduction in the amount of retained (second) polypeptide in the presence of a candidate compound compared to that in its absence indicates that the compound inhibits an AIB1/ER interaction. Techniques for column chromatography and coprecipitation of polypeptides are well known in the art.

An evaluation of AIB1/ER interaction and identification of compounds that blocks or reduces the interaction can also be carried out in vivo using a yeast two-hybrid expression system in which the activity of a transcriptional activator is reconstituted when the two proteins or polypeptides of interest closely interact or bind to one another.

The yeast GAL4 protein consists of functionally distinguishable domains. One domain is responsible for DNA-binding and the other for transcriptional activation. In the two-hybrid expression system, plasmids encoding two hybrid proteins, a first fusion protein containing the GAL4 DNA-binding domain fused to a first protein, e.g., AIB1, and the second fusion protein containing the GAL4 activation domain fused to a second protein, e.g., ER, are introduced into yeast. If the two proteins are able to interact with one another, the ability to activate transcription from promoters containing Gal4-binding sites upstream from an activating sequence from GAL1 ($UAS_G$) is reconstituted leading to the expression of a reporter gene. A reduction in the expression of the reporter gene in the presence of a candidate compound compared to that in the absence of the compound indicates that the compound reduces an AIB1/ER interaction.

A method of identifying a DNA-binding protein which regulates AIB1 transcription can be carried out as follows: A DNA containing a cis-acting regulatory element can be immobilized on polymeric beads, such as agarose or acrylamide. A mixture of proteins, such as a cell lysate, is allowed to come in contact with and bind to the DNA. Following removal of non-binding proteins, specifically-bound proteins, are eluted with a competing DNA sequence which may be identical to the immobilized sequence. Specific binding of a protein to the DNA regulatory element indicates that the protein may regulate AIB1 transcription. Functional activity of the identified trans-acting factor can be confirmed with an appropriate functional assay, such as one which measures the level of transcription of a reporter gene having the cis-acting regulatory gene 5' to the transcription start site of AIB1.

A method of identifying a compound which decreases the level of AIB1 transcription can be accomplished by contacting an immobilized AIB1-derived cis-acting regulatory element with a trans-acting regulatory factor in the presence and absence of candidate compound. A detectable change, i.e., a reduction, in specific binding of the trans-acting factor to its DNA target indicates that the candidate compound inhibits AIB1 transcription.

In addition to interacting with ER, AIB1 also interacts with the transcriptional integrators CBP and p300. CBP and p300 participate in the basal transcriptional apparatus in a cell. Thus, another approach to inhibit signal transduction through AIB1 is to prevent the formation of or disrupt an interaction of AIB1 with CBP and/or p300. Compounds which inhibit signal transduction (and therefore cell proliferation) can be identified by contacting AIB1 (or a fragment thereof which interacts with CBP or p300) with CBP or p300 (or a fragment thereof containing an AIB1-interacting domain, e.g., a C-terminal fragment) in the presence and absence of a candidate compound. For example, a C-terminal fragment of CBP involved in steroid receptor co-activator interaction contains 105 amino acids in the Q-rich region of CBP (Kamci et al., 1996, Cell 85:403–414; Yao et al., 1996, Proc. Natl. Acad. Sci. USA 93:10626–10631; Hanstein et al., 1996, Proc. Natl. Acad. Sci. USA 93:11540–11545). A decrease in AIB1 interaction with CBP or p300 in the presence of a candidate compound compared to that its absence indicates that the compound inhibits AIB1 interaction with these transcriptional integrators, and as a result, AIB1-mediated signal transduction leading to DNA transcription and cell proliferation. Compounds which inhibit AIB1 interaction with transcriptional integrators can also be identified using a co-precipitation assay and the yeast two-hybrid expression system described above.

B. In Vivo Assays

Transgenic mice are made by standard methods, e.g., as described in Leder et al., U.S. Pat. No. 4,736,866, herein incorporated by reference, or Hogan et al., 1986 Manipulating the Mouse Embryo. Cold Spring Harbor Laboratory" New York.

Briefly, a vector containing a promoter operably linked to AIB1-encoding cDNA is injected into murine zygotes, e.g., C57BL/6J X DBA/2F2 zygotes. Incorporation of the transgene into murine genomic DNA is monitored using methods well known in the art of molecular biology, e.g., dot blotting tail DNA with a probe complimentary to the 3' region of the gene contained in the AIB1 transgene construct. Mice thus confirmed to harbor the transgene can then be used as founders. Animal lines are created by crossing founders with C57BL/6J mice (The Jackson Laboratory, Bar Harbor, Me.). AIB1 transgenic mice can be used to screen candidate compounds in vivo to identify compounds which inhibit aberrant cell proliferation, e.g., as measured by reduction tumor growth or metastasis. AIB1 transgenic mice are also useful to identify other genes involved in steroid hormone receptor-dependent cancers and to establish mouse cell lines which overexpress AIB1. AIB1-overexpressing cell lines are useful to screen for compounds that interfere with AIB1 function, e.g, by blocking the interaction of AIB1 with a ligand.

EXAMPLE 6

AIB1 Therapy

As discussed above, AIB1 is a novel member of the SRC-1 family of transcriptional co-activators. Amplification and overexpression of AIB1 in ER-positive breast and ovarian cancer cells and in breast cancer biopsies implicate this protein as a critical component of the estrogen response pathway. AIB1 overexpression results in increased ER-dependent transcriptional activity which confers a growth advantage of AIB1 amplification-bearing clones during the development and progression of estrogen-dependent cancers.

Compounds which inhibit or disrupt the interaction of an AIB1 gene product with a steroid hormone receptor, e.g., ER, are useful as anti-neoplastic agents for the treatment of patients suffering from steroid hormone-responsive cancers such as breast cancer, ovarian cancer, prostate cancer, and colon cancer. Likewise, compounds which disrupt interaction between AIB1 and p300 and/or CBP are also useful as anti-neoplastic agents.

AIB1 polypeptides or peptide mimetics of such polypeptides, e.g., those containing domains which interact with steroid hormone receptors, can be administered to patients to block the interaction of endogenous intracellular AIB1 and a steroid hormone receptor, e.g., ER in an aberrantly proliferating cell. A mimetic may be made by introducing conservative amino acid substitutions into the peptide. Certain amino acid substitutions arc conservative since the old and the new amino acid share a similar hydrophobicity or hydrophylicity or are similarly acidic, basic or neutrally charged (Stryer "Biocbemistry" 1975, Ch.2, Freeman and Company, New York). Conservative substitutions replace one amino acid with another amino acid that is similar in size, hydrophobicity, etc. Examples of conservative substitutions are shown in the table below (Table 1).

TABLE 1

| Original Residue | Conservative Substitutions |
| --- | --- |
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Variations in the cDNA sequence that result in amino acid changes, whether conservative or not, should be minimized in order to preserve the functional and immunologic identity of the encoded protein.

Compositions administered therapeutically include polypeptide mimetics in which one or more peptide bonds have been replaced with an alternative type of covalent bond which is not susceptible to cleavage by peptidases. Where proteolytic degradation of the peptides following injection into the subject is a problem, replacement of a particularly sensitive peptide bond with a noncleavable peptide mimetic yields a more stable and thus more useful therapeutic polypeptide. Such mimetics, and methods of incorporating them into polypeptides, are well known in the art. Similarly, the replacement of an L-amino acid residue with a D-amino acid residue is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl.

AIB1 polypeptides or related peptide mimetics may be administered to a patient intravenously in a pharmaceutically acceptable carrier such as physiological saline. Standard methods for intracellular delivery of peptides can be used, e.g. packaged in liposomes. Such methods are well known to those of ordinary skill in the art. It is expected that an intravenous dosage of approximately 1 to 100 μmoles of the polypeptide of the invention would be administered per kg of body weight per day. The compositions of the invention are useful for parenteral administration, such as intravenous, subcutaneous, intramuscular, and intraperitoneal.

The therapeutic compositions of this invention may also be administered by the use of surgical implants which release the compounds of the invention. These devices could be readily implanted into the target tissue, e.g., a solid tumor mass, and could be mechanical or passive. Mechanical devices, such as pumps, are well known in the art, as are passive devices (e.g., consisting of a polymer matrix which contains therapeutic formulations; these polymers may slowly dissolve or degrade to release the compound, or may be porous and allow release via pores).

Antisense therapy in which a DNA sequence complementary to an AIB1 mRNA transcript is either produced in the cell or administered to the cell can be used to decrease AIB1 gene expression thereby inhibiting undesired cell proliferation, e.g., proliferation of steroid hormone-responsive cancer cells. An antisense polynucleotide, i.e., one which is complementary of the coding sequence of the AIB1 gene, is introduced into the cells in which the gene is overproduced. The antisense strand (either RNA or DNA) may be directly introduced into the cells in a form that is capable of binding to the transcripts. Alternatively, a vector containing a DNA sequence which, once within the target cells, is transcribed into the appropriate antisense mRNA, may be administered. An antisense nucleic acid which hybridizes to the coding strand of AIB1 DNA can decrease or inhibit production of an AIB1 gene product by associating with the normally single-stranded MRNA transcript, and thereby, interfering with translation.

DNA is introduced into target cells of the patient with or without a vector or using standard vectors and/or gene delivery systems. Suitable gene delivery systems may include liposomes, receptor-mediated delivery systems, naked DNA, and viral vectors such as herpes viruses, retroviruses, and adenoviruses, among others. The DNA of the invention may be administered in a pharmaceutically acceptable carrier. Pharmaceutically acceptable carriers are biologically compatible vehicles which are suitable for administration to an animal e.g., physiological saline. A therapeutically effective amount is an amount of the nucleic acid of the invention which is capable of producing a medically desirable result in a patient. As is well known in the medical arts, dosage for any given patient depends upon many factors, including the patient's size, body surface area, age, the particular compound to be administered, sex, time and route of administration, general health, and other drugs being administered concurrently. Dosages will vary, but a preferred dosage for intravenous administration of a nucleic acid is from approximately $10^6$ to $10^{22}$ copies of the nucleic acid molecule.

Determination of optimal dosage is well within the abilities of a pharmacologist of ordinary skill.

EXAMPLE 7

AIB1 Knockout and Overexpression Mouse Mutants

Mutants organism that underexpress or overexpress AIB1 are useful for research. Such mutants allow insight into the physiological and/or pathological role of AIB1 in a healthy and/or pathological organism. These mutants are said to be "genetically engineered," meaning that information in the form of nucleotides has been transferred into the mutant's genome at a location, or in a combination, in which it would not normally exist. Nucleotides transferred in this way are said to be "non-native." For example, a WAP promoter inserted upstream of a native AIB1 gene would be non-native. An extra copy of a mouse AIB1 gene present on a plasmid and transformed into a mouse cell would be non-native. Mutants may be, for example, produced from mammals, such as mice, that either overexpress AIB1 or underexpress AIB1 or that do not express AIB1 at all. Overexpression mutants are made by increasing the number of AIB1 genes in the organism, or by introducing an AIB1 gene into the organism under the control of a constitutive or inducible or viral promoter such as the mouse mammary tumor virus (MMTV) promoter or the whey acidic protein (WAP) promoter or the metallothionein promoter. Mutants that underexpress AIB1 may be made by using an inducible or repressible promoter, or by deleting the AIB1 gene, or by destroying or limiting the function of the AIB1 gene, for instance by disrupting the gene by transposon insertion.

Anti-sense genes may be engineered into the organism, under a constitutive or inducible promoter, to decrease or prevent AIB1 expression. A gene is said to be "functionally deleted" when genetic engineering has been used to negate or reduce gene expression to negligible levels. When a mutant is referred to in this application as having the AIB1 gene altered or functionally deleted, this reference refers to the AIB1 gene and to any ortholog of this gene, for instance "a transgenic animal wherein at least one AIB1 gene has been functionally deleted" would encompass the mouse ortholog of the AIB1 gene, pCIP. When a mutant is referred to as having "more than the normal copy number" of a gene, this means that it has more than the usual number of genes found in the wild-type organism, eg: in the diploid mouse or human.

A mutant mouse overexpressing AIB1 may be made by constructing a plasmid having the AIB1 gene driven by a promoter, such as the mouse mammary tumor virus (MMTV) promoter or the whey acidic protein (WAP) promoter. This plasmid may be introduced into mouse oocytes by microinjection. The oocytes are implanted into pseudopregnant females, and the litters are assayed for insertion of the transgene. Multiple strains containing the transgene are then available for study.

WAP is quite specific for mammary gland expression during lactation, and MMTV is expressed in a variety of tissues including mammary gland, salivary gland and lymphoid tissues. Many other promoters might be used to achieve various patterns of expression, e.g., the metallothionein promoter.

An inducible system may be created in which AIB1 is driven by a promoter regulated by an agent which can be fed to the mouse such as tetracycline. Such techniques are well known in the art.

A mutant knockout mouse from which the AIB1 (also called pCIP) gene is deleted was made by removing coding regions of the AIB1 gene from mouse embryonic stem cells. FIG. 5 shows the intron/exon structure for pCIP. Using this table, mutations can be targeted to coding sequences, avoiding silent mutations caused by deletion of non-coding sequences. (FIG. 6 shows the intron/exon structure for the human AIB1 gene). These cells were microinjected into mouse embryos leading to the deletion of the mouse AIB1 gene in the germ line of a transgenic mouse. The mouse AIB1 gene was mapped and isolated by the following method: The primers AIB/mEST F1 (5'-TCCTTTTCCCAGCAGCAGTTTG-3'; SEQ.I.D. 10) and AIB1/mEST R1 (5'-ATGCCAGACATGGGCATGGG-3' SEQ.I.D.11) were used to screen a mouse Bacterial Artificial Chromosome (BAC) library and to isolate a mouse BAC (designated 195H10). This BAC was assigned to mouse chromosome 2 by fluorescence in situ hybridization (FISH). This region is the mouse equivalent of the portion of human chromosome which carries AIB1.

Figure 4:
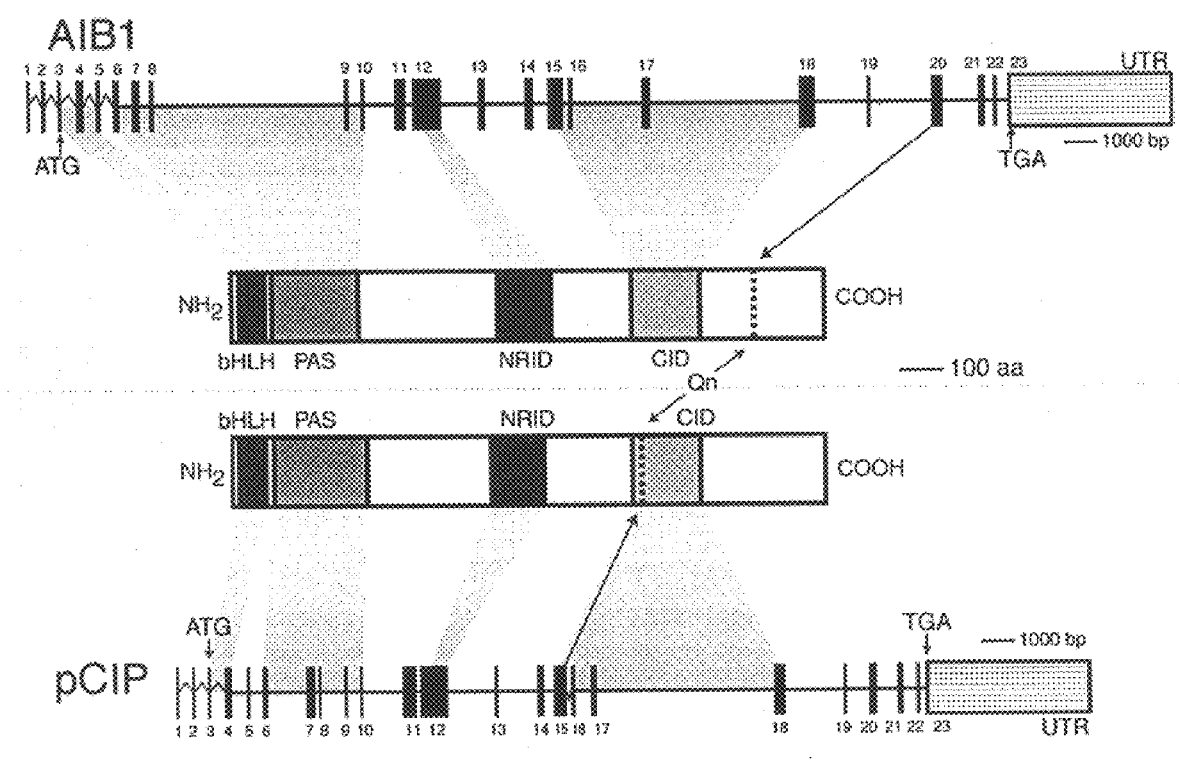
FIG. 4 is a schematic diagram comparing the DNA and protein structures of pCIP (the mouse ortholog of AIB1) and the human AIB1; exons are shown as black boxes.

To map the structure of the gene, first the structure of the human AIB1 gene was determined by polymerase chain reaction of a human genomic DNA clone containing AIB1 using standard methods (Genomics Jan 20, 25, 1995 (2):501–506) and then the sequences of the intron exon boundaries were determined (FIG. 4). Based on this information, the corresponding regions of the mouse BAC were sequenced. The structure of the mouse gene corresponds closely to that of the human gene (FIG. 4). This information localizes the coding regions of the mouse AIB1 gene so that a targeting vector can be constructed to remove these regions from mouse embryonic stem cells. These cells can be then injected into mouse embryos leading to deletion of the mouse AIB1 gene in the germ line of a transgenic mouse. The methods of creating deletion mutations by using a targeting vector have been described in Cell (Thomas and Capecch, Cell 51(3):503–512, 1987).

References and patents referred to herein are incorporated by reference.

The above examples are provided by way of illustration only and are in no way intended to limit the scope of the invention. One of skill in tie art will see that the invention may be modified in various ways without departing from the spirit or principle of the invention. We claim all such modifications.

What is claimed is:

1. An isolated AIB1 polypeptide comprising SEQ ID NO: 8, wherein the polypeptide acts as a co-activator of an estrogen receptor.

2. A method of identifying a candidate compound which may inhibit estrogen receptor (ER)-dependent transcription comprising
   contacting the compound with the AIB1 polypeptide of claim 1 and
   determining whether the compound binds to the polypeptide,
   wherein binding of the compound to the polypeptide indicates that the compound may inhibit ER-dependent transcription.

3. The method of claim 2, wherein the AIB1 polypeptide comprises an amino acid sequence as set forth as SEQ ID NO: 2.

4. A method of claim 2, wherein the AIB1 polypeptide comprises an amino acid sequence as set forth as SEQ ID NO: 3.

5. A method of identifying a candidate compound which may inhibit estrogen receptor-dependent transcription comprising:
   contacting the AIB1 polypeptide of claim 1 and an estrogen receptor polypeptide with the compound and
   determining the ability of the compound to interfere with the binding of the estrogen receptor polypeptide with the AIB1 polypeptide,
   wherein interference of the binding of the estrogen receptor polypeptide and the AIB1 polypeptide indicates the compound may inhibit estrogen receptor dependent transcription.

6. The method of claim 5, wherein the AIB polypeptide further comprises SEQ ID NO: 2.

7. The method of claim 5, wherein the AIB polypeptide further comprises SEQ ID NO: 3.

8. An isolated DNA comprising a sequence encoding a AIB1 polypeptide comprising SEQ ID NO: 8, wherein the polypeptide acts as co-activator of an estrogen receptor.

9. The isolated DNA of claim 8, wherein the AIB1 polypeptide is a human AIB1 polypeptide.

10. The isolated DNA of claim 8, wherein the polypeptide comprises the amino acid sequence of SEQ ID NO: 4.

11. The isolated DNA of claim 8, wherein the polypeptide further comprises the amino acid sequence of SEQ ID NO: 2.

12. The isolated DNA of claim 8, wherein the AIB1 polypeptide further comprises the amino acid sequence of SEQ ID NO: 3.

13. An isolated polynucleotide comprising a nucleic acid sequence set forth as (a) SEQ ID NO: 1, (b) a degenerate variant thereof, or (c) the complement thereof.

14. The isolated DNA of claim 8, operably linked to a promoter.

15. An isolated host cell comprising the DNA of claim 8.

16. An isolated polynucleotide having at least 90% homology to SEQ ID NO: 1, wherein the polynucleotide encodes a polypeptide that acts as a co-activator of an estrogen receptor.

17. The isolated polypeptide of claim 1, wherein the polypeptide further comprises SEQ ID NO: 2.

18. The isolated polypeptide of claim 1, wherein the polypeptide further comprises SEQ ID NO: 3.

19. The isolated polypeptide of claim 17, wherein the polypeptide further comprises SEQ ID NO: 3.

20. The isolated polypeptide of claim 1, wherein the polypeptide comprises SEQ ID NO: 4.

21. An isolated polypeptide fragment of SEQ ID NO: 4, wherein the polypeptide fragment comprises SEQ ID NO: 8, and wherein the polypeptide fragment binds the estrogen receptor.

22. An isolated nucleic acid sequence encoding the polypeptide of claim 21.

23. An isolated nucleic acid sequence encoding the polypeptide of claim 20.

24. The isolated nucleic acid encoding the polypeptide of claim 13, wherein the nucleic acid comprises a sequence set forth as SEQ ID NO: 1.

25. An isolated polynucleotide comprising a sequence set forth as SEQ ID NO: 1, a degenerate variant thereof, or the complement thereof.

26. The isolated polynucleotide of claim 16, wherein the polynucleotide has at least 95% homology to SEQ ID NO: 1, wherein the polynucleotide encodes a polypeptide that acts as a co-activator of an estrogen receptor.

27. The isolated polynucleotide of claim 16, wherein the polynucleotide has at least 98% homology to SEQ ID NO: 1, wherein the polynucleotide encodes a polypeptide that acts as a co-activator of an estrogen receptor.

28. An isolated polypeptide encoded by the polynucleotide of claim 26.

29. An isolated polypeptide encoded by the polynucleotide of claim 27.

30. An isolated polynucleotide comprising a nucleic acid sequence encoding a polypeptide comprising SEQ ID NO: 8, wherein the polypeptide acts as co-activator of an estrogen receptor, wherein the polynucleotide hybridizes under high stringency conditions to a nucleic acid having a sequence as set forth as SEQ ID NO: 1, or the complement thereof, and wherein high stringency conditions comprise hybridization at about 42° C. and about 50% formamide, a first wash at 65° C., about 2×SSC and 1% SDS; followed by a second wash at about 65° C. and about 0.1×SSC.

* * * * *

UNITED STATES PATENT AND TRADEMARK OFFICE
CERTIFICATE OF CORRECTION

PATENT NO. : 6,562,589 B1
DATED : May 13, 2003
INVENTOR(S) : Meltzer et al.

It is certified that error appears in the above-identified patent and that said Letters Patent is hereby corrected as shown below:

Column 2,
Line 53, "idertify cells" should read -- identify cells --.
Line 54, "arc" should read -- are --.

Column 4,
Line 8, "contaig" should read -- containing --.
Line 32, "Per/Amt/Sim" should read -- Per/Arnt/Sim --.

Column 9,
Line 10, "co-ctivator" should read -- co-activator --.

Column 13,
Line 47, "an be" should read -- can be --.

Column 15,
Line 26 "anti-strogen" should read -- anti-estrogen --.
Line 29, "in sits)" should read -- in situ) --.
Line 32, "arc" should read -- are --.
Line 37, "polygonal" should read -- polyclonal --.

Column 18,
Line 8, "(Kamci" should read -- (Kamei --.

Column 19,
Line 8, "arc" should read -- are --.
Line 11, "Biocbemistry" should read -- Biochemistry --.

Column 20,
Line 30, "MRNA" should read -- mRNA --.

UNITED STATES PATENT AND TRADEMARK OFFICE
CERTIFICATE OF CORRECTION

PATENT NO. : 6,562,589 B1
DATED : May 13, 2003
INVENTOR(S) : Meltzer et al.

It is certified that error appears in the above-identified patent and that said Letters Patent is hereby corrected as shown below:

Column 22,
Line 23, "chromosome which" should read -- chromosome 20 which --.
Line 46, "tie art" should read -- the art --.

Signed and Sealed this

Fourth Day of November, 2003

JAMES E. ROGAN
*Director of the United States Patent and Trademark Office*

SEQUENCE LISTING

```
<160> NUMBER OF SEQ ID NOS:  12

<210> SEQ ID NO 1
<211> LENGTH: 6835
<212> TYPE: DNA
<213> ORGANISM: Homo sapiens
<220> FEATURE:
<221> NAME/KEY: CDS
<222> LOCATION: (201)..(4463)

<400> SEQUENCE: 1
cggcggcggc tgcggcttag tcggtggcgg ccggcggcgg ctgcgggctg agcggcgagt      60
```

-continued

```
ttccgattta aagctgagct gcgaggaaaa tggcggcggg aggatcaaaa tacttgctgg         120
atggtggact cagagaccaa taaaaataaa ctgcttgaac atcctttgac tggttagcca         180
gttgctgatg tatattcaag atg agt gga tta gga gaa aac ttg gat cca ctg        233
                      Met Ser Gly Leu Gly Glu Asn Leu Asp Pro Leu
                       1               5                  10 gcc agt gat tca cga aaa cgc aaa ttg cca tgt gat act cca gga caa           281
Ala Ser Asp Ser Arg Lys Arg Lys Leu Pro Cys Asp Thr Pro Gly Gln
             15                  20                  25 ggt ctt acc tgc agt ggt gaa aaa cgg aga cgg gag cag gaa agt aaa           329
Gly Leu Thr Cys Ser Gly Glu Lys Arg Arg Arg Glu Gln Glu Ser Lys
         30                  35                  40 tat att gaa gaa ttg gct gag ctg ata tct gcc aat ctt agt gat att           377
Tyr Ile Glu Glu Leu Ala Glu Leu Ile Ser Ala Asn Leu Ser Asp Ile
 45                  50                  55 gac aat ttc aat gtc aaa cca gat aaa tgt gcg att tta aag gaa aca           425
Asp Asn Phe Asn Val Lys Pro Asp Lys Cys Ala Ile Leu Lys Glu Thr
 60                  65                  70                  75 gta aga cag ata cgt caa ata aaa gag caa gga aaa act att tcc aat           473
Val Arg Gln Ile Arg Gln Ile Lys Glu Gln Gly Lys Thr Ile Ser Asn
                 80                  85                  90 gat gat gat gtt caa aaa gcc gat gta tct tct aca ggg cag gga gtt           521
Asp Asp Asp Val Gln Lys Ala Asp Val Ser Ser Thr Gly Gln Gly Val
             95                 100                 105 att gat aaa gac tcc tta gga ccg ctt tta ctt cag gca ttg gat ggt           569
Ile Asp Lys Asp Ser Leu Gly Pro Leu Leu Leu Gln Ala Leu Asp Gly
        110                 115                 120 ttc cta ttt gtg gtg aat cga gac gga aac att gta ttt gta tca gaa           617
Phe Leu Phe Val Val Asn Arg Asp Gly Asn Ile Val Phe Val Ser Glu
    125                 130                 135 aat gtc aca caa tac ctg caa tat aag caa gag gac ctg gtt aac aca           665
Asn Val Thr Gln Tyr Leu Gln Tyr Lys Gln Glu Asp Leu Val Asn Thr
140                 145                 150                 155 agt gtt tac aat atc tta cat gaa gaa gac aga aag gat ttt ctt aag           713
Ser Val Tyr Asn Ile Leu His Glu Glu Asp Arg Lys Asp Phe Leu Lys
                160                 165                 170 aat tta cca aaa tct aca gtt aat gga gtt tcc tgg aca aat gag acc           761
Asn Leu Pro Lys Ser Thr Val Asn Gly Val Ser Trp Thr Asn Glu Thr
            175                 180                 185 caa aga caa aaa agc cat aca ttt aat tgc cgt atg ttg atg aaa aca           809
Gln Arg Gln Lys Ser His Thr Phe Asn Cys Arg Met Leu Met Lys Thr
        190                 195                 200 cca cat gat att ctg gaa gac ata aac gcc agt cct gaa atg cgc cag           857
Pro His Asp Ile Leu Glu Asp Ile Asn Ala Ser Pro Glu Met Arg Gln
    205                 210                 215 aga tat gaa aca atg cag tgc ttt gcc ctg tct cag cca cga gct atg           905
Arg Tyr Glu Thr Met Gln Cys Phe Ala Leu Ser Gln Pro Arg Ala Met
220                 225                 230                 235 atg gag gaa ggg gaa gat ttg caa tct tgt atg atc tgt gtg gca cgc           953
Met Glu Glu Gly Glu Asp Leu Gln Ser Cys Met Ile Cys Val Ala Arg
                240                 245                 250 cgc att act aca gga gaa aga aca ttt cca tca aac cct gag agc ttt          1001
Arg Ile Thr Thr Gly Glu Arg Thr Phe Pro Ser Asn Pro Glu Ser Phe
            255                 260                 265 att acc aga cat gat ctt tca gga aag gtt gtc aat ata gat aca aat          1049
Ile Thr Arg His Asp Leu Ser Gly Lys Val Val Asn Ile Asp Thr Asn
        270                 275                 280 tca ctg aga tcc tcc atg agg cct ggc ttt gaa gat ata atc cga agg          1097
Ser Leu Arg Ser Ser Met Arg Pro Gly Phe Glu Asp Ile Ile Arg Arg
    285                 290                 295
```

```
tgt att cag aga ttt ttt agt cta aat gat ggg cag tca tgg tcc cag      1145
Cys Ile Gln Arg Phe Phe Ser Leu Asn Asp Gly Gln Ser Trp Ser Gln
300                 305                 310                 315 aaa cgt cac tat caa gaa gct tat ctt aat ggc cat gca gaa acc cca      1193
Lys Arg His Tyr Gln Glu Ala Tyr Leu Asn Gly His Ala Glu Thr Pro
                320                 325                 330 gta tat cga ttc tcg ttg gct gat gga act ata gtg act gca cag aca      1241
Val Tyr Arg Phe Ser Leu Ala Asp Gly Thr Ile Val Thr Ala Gln Thr
            335                 340                 345 aaa agc aaa ctc ttc cga aat cct gta aca aat gat cga cat ggc ttt      1289
Lys Ser Lys Leu Phe Arg Asn Pro Val Thr Asn Asp Arg His Gly Phe
        350                 355                 360 gtc tca acc cac ttc ctt cag aga gaa cag aat gga tat aga cca aac      1337
Val Ser Thr His Phe Leu Gln Arg Glu Gln Asn Gly Tyr Arg Pro Asn
    365                 370                 375 cca aat cct gtt gga caa ggg att aga cca cct atg gct gga tgc aac      1385
Pro Asn Pro Val Gly Gln Gly Ile Arg Pro Pro Met Ala Gly Cys Asn
380                 385                 390                 395 agt tcg gta ggc ggc atg agt atg tcg cca aac caa ggc tta cag atg      1433
Ser Ser Val Gly Gly Met Ser Met Ser Pro Asn Gln Gly Leu Gln Met
                400                 405                 410 ccg agc agc agg gcc tat ggc ttg gca gac cct agc acc aca ggg cag      1481
Pro Ser Ser Arg Ala Tyr Gly Leu Ala Asp Pro Ser Thr Thr Gly Gln
            415                 420                 425 atg agt gga gct agg tat ggg ggt tcc agt aac ata gct tca ttg acc      1529
Met Ser Gly Ala Arg Tyr Gly Gly Ser Ser Asn Ile Ala Ser Leu Thr
        430                 435                 440 cct ggg cca ggc atg caa tca cca tct tcc tac cag aac aac aac tat      1577
Pro Gly Pro Gly Met Gln Ser Pro Ser Ser Tyr Gln Asn Asn Asn Tyr
    445                 450                 455 ggg ctc aac atg agt agc ccc cca cat ggg agt cct ggt ctt gcc cca      1625
Gly Leu Asn Met Ser Ser Pro Pro His Gly Ser Pro Gly Leu Ala Pro
460                 465                 470                 475 aac cag cag aat atc atg att tct cct cgt aat cgt ggg agt cca aag      1673
Asn Gln Gln Asn Ile Met Ile Ser Pro Arg Asn Arg Gly Ser Pro Lys
                480                 485                 490 ata gcc tca cat cag ttt tct cct gtt gca ggt gtg cac tct ccc atg      1721
Ile Ala Ser His Gln Phe Ser Pro Val Ala Gly Val His Ser Pro Met
            495                 500                 505 gca tct tct ggc aat act ggg aac cac agc ttt tcc agc agc tct ctc      1769
Ala Ser Ser Gly Asn Thr Gly Asn His Ser Phe Ser Ser Ser Ser Leu
        510                 515                 520 agt gcc ctg caa gcc atc agt gaa ggt gtg ggg act tcc ctt tta tct      1817
Ser Ala Leu Gln Ala Ile Ser Glu Gly Val Gly Thr Ser Leu Leu Ser
    525                 530                 535 act ctg tca tca cca ggc ccc aaa ttg gat aac tct ccc aat atg aat      1865
Thr Leu Ser Ser Pro Gly Pro Lys Leu Asp Asn Ser Pro Asn Met Asn
540                 545                 550                 555 att acc caa cca agt aaa gta agc aat cag gat tcc aag agt cct ctg      1913
Ile Thr Gln Pro Ser Lys Val Ser Asn Gln Asp Ser Lys Ser Pro Leu
                560                 565                 570 ggc ttt tat tgc gac caa aat cca gtg gag agt tca atg tgt cag tca      1961
Gly Phe Tyr Cys Asp Gln Asn Pro Val Glu Ser Ser Met Cys Gln Ser
            575                 580                 585 aat agc aga gat cac ctc agt gac aaa gaa agt aag gag agc agt gtt      2009
Asn Ser Arg Asp His Leu Ser Asp Lys Glu Ser Lys Glu Ser Ser Val
        590                 595                 600 gag ggg gca gag aat caa agg ggt cct ttg gaa agc aaa ggt cat aaa      2057
Glu Gly Ala Glu Asn Gln Arg Gly Pro Leu Glu Ser Lys Gly His Lys
```

```
                605                  610                 615
aaa tta ctg cag tta ctt acc tgt tct tct gat gac cgg ggt cat tcc      2105
Lys Leu Leu Gln Leu Leu Thr Cys Ser Ser Asp Asp Arg Gly His Ser
620                 625                 630                 635 tcc ttg acc aac tcc ccc cta gat tca agt tgt aaa gaa tct tct gtt      2153
Ser Leu Thr Asn Ser Pro Leu Asp Ser Ser Cys Lys Glu Ser Ser Val
                640                 645                 650 agt gtc acc agc ccc tct gga gtc tcc tcc tct aca tct gga gga gta      2201
Ser Val Thr Ser Pro Ser Gly Val Ser Ser Ser Thr Ser Gly Gly Val
            655                 660                 665 tcc tct aca tcc aat atg cat ggg tca ctg tta caa gag aag cac cgg      2249
Ser Ser Thr Ser Asn Met His Gly Ser Leu Leu Gln Glu Lys His Arg
        670                 675                 680 att ttg cac aag ttg ctg cag aat ggg aat tca cca gct gag gta gcc      2297
Ile Leu His Lys Leu Leu Gln Asn Gly Asn Ser Pro Ala Glu Val Ala
685                 690                 695 aag att act gca gaa gcc act ggg aaa gac acc agc agt ata act tct      2345
Lys Ile Thr Ala Glu Ala Thr Gly Lys Asp Thr Ser Ser Ile Thr Ser
700                 705                 710                 715 tgt ggg gac gga aat gtt gtc aag cag gag cag cta agt cct aag aag      2393
Cys Gly Asp Gly Asn Val Val Lys Gln Glu Gln Leu Ser Pro Lys Lys
                720                 725                 730 aag gag aat aat gca ctt ctt aga tac ctg ctg gac agg gat gat cct      2441
Lys Glu Asn Asn Ala Leu Leu Arg Tyr Leu Leu Asp Arg Asp Asp Pro
            735                 740                 745 agt gat gca ctc tct aaa gaa cta cag ccc caa gtg gaa gga gtg gat      2489
Ser Asp Ala Leu Ser Lys Glu Leu Gln Pro Gln Val Glu Gly Val Asp
        750                 755                 760 aat aaa atg agt cag tgc acc agc tcc acc att cct agc tca agt caa      2537
Asn Lys Met Ser Gln Cys Thr Ser Ser Thr Ile Pro Ser Ser Ser Gln
765                 770                 775 gag aaa gac cct aaa att aag aca gag aca agt gaa gag gga tct gga      2585
Glu Lys Asp Pro Lys Ile Lys Thr Glu Thr Ser Glu Glu Gly Ser Gly
                780                 785                 790                 795 gac ttg gat aat cta gat gct att ctt ggt gat ctg act agt tct gac      2633
Asp Leu Asp Asn Leu Asp Ala Ile Leu Gly Asp Leu Thr Ser Ser Asp
                        800                 805                 810 ttt tac aat aat tcc ata tcc tca aat ggt agt cat ctg ggg act aag      2681
Phe Tyr Asn Asn Ser Ile Ser Ser Asn Gly Ser His Leu Gly Thr Lys
            815                 820                 825 caa cag gtg ttt caa gga act aat tct ctg ggt ttg aaa agt tca cag      2729
Gln Gln Val Phe Gln Gly Thr Asn Ser Leu Gly Leu Lys Ser Ser Gln
        830                 835                 840 tct gtg cag tct att cgt cct cca tat aac cga gca gtg tct ctg gat      2777
Ser Val Gln Ser Ile Arg Pro Pro Tyr Asn Arg Ala Val Ser Leu Asp
845                 850                 855 agc cct gtt tct gtt ggc tca agt cct cca gta aaa aat atc agt gct      2825
Ser Pro Val Ser Val Gly Ser Ser Pro Pro Val Lys Asn Ile Ser Ala
860                 865                 870                 875 ttc ccc atg tta cca aag caa ccc atg ttg ggt ggg aat cca aga atg      2873
Phe Pro Met Leu Pro Lys Gln Pro Met Leu Gly Gly Asn Pro Arg Met
                880                 885                 890 atg gat agt cag gaa aat tat ggc tca agt atg ggt ggg cca aac cga      2921
Met Asp Ser Gln Glu Asn Tyr Gly Ser Ser Met Gly Gly Pro Asn Arg
            895                 900                 905 aat gtg act gtg act cag act cct tcc tca gga gac tgg ggc tta cca      2969
Asn Val Thr Val Thr Gln Thr Pro Ser Ser Gly Asp Trp Gly Leu Pro
        910                 915                 920 aac tca aag gcc ggc aga atg gaa cct atg aat tca aac tcc atg gga      3017
```

```
Asn Ser Lys Ala Gly Arg Met Glu Pro Met Asn Ser Asn Ser Met Gly
    925                 930                 935 aga cca gga gga gat tat aat act tct tta ccc aga cct gca ctg ggt    3065
Arg Pro Gly Gly Asp Tyr Asn Thr Ser Leu Pro Arg Pro Ala Leu Gly
940                 945                 950                 955 ggc tct att ccc aca ttg cct ctt cgg tct aat agc ata cca ggt gcg    3113
Gly Ser Ile Pro Thr Leu Pro Leu Arg Ser Asn Ser Ile Pro Gly Ala
            960                 965                 970 aga cca gta ttg caa cag cag cag atg ctt caa atg agg cct ggt        3161
Arg Pro Val Leu Gln Gln Gln Gln Met Leu Gln Met Arg Pro Gly
        975                 980                 985 gaa atc ccc atg gga atg ggg gct aat ccc tat ggc caa gca gca gca    3209
Glu Ile Pro Met Gly Met Gly Ala Asn Pro Tyr Gly Gln Ala Ala Ala
    990                 995                 1000 tct aac caa ctg ggt tcc tgg ccc gat ggc atg ttg tcc atg gaa caa    3257
Ser Asn Gln Leu Gly Ser Trp Pro Asp Gly Met Leu Ser Met Glu Gln
    1005                1010                1015 gtt tct cat ggc act caa aat agg cct ctt ctt agg aat tcc ctg gat    3305
Val Ser His Gly Thr Gln Asn Arg Pro Leu Leu Arg Asn Ser Leu Asp
1020                1025                1030                1035 gat ctt gtt ggg cca cct tcc aac ctg gaa ggc cag agt gac gaa aga    3353
Asp Leu Val Gly Pro Pro Ser Asn Leu Glu Gly Gln Ser Asp Glu Arg
            1040                1045                1050 gca tta ttg gac cag ctg cac act ctt ctc agc aac aca gat gcc aca    3401
Ala Leu Leu Asp Gln Leu His Thr Leu Leu Ser Asn Thr Asp Ala Thr
        1055                1060                1065 ggc ctg gaa gaa att gac aga gct ttg ggc att cct gaa ctt gtc aat    3449
Gly Leu Glu Glu Ile Asp Arg Ala Leu Gly Ile Pro Glu Leu Val Asn
    1070                1075                1080 cag gga cag gca tta gag ccc aaa cag gat gct ttc caa ggc caa gaa    3497
Gln Gly Gln Ala Leu Glu Pro Lys Gln Asp Ala Phe Gln Gly Gln Glu
    1085                1090                1095 gca gca gta atg atg gat cag aag gca gga tta tat gga cag aca tac    3545
Ala Ala Val Met Met Asp Gln Lys Ala Gly Leu Tyr Gly Gln Thr Tyr
1100                1105                1110                1115 cca gca cag ggg cct cca atg caa gga ggc ttt cat ctt cag gga caa    3593
Pro Ala Gln Gly Pro Pro Met Gln Gly Gly Phe His Leu Gln Gly Gln
            1120                1125                1130 tca cca tct ttt aac tct atg atg aat cag atg aac cag caa ggc aat    3641
Ser Pro Ser Phe Asn Ser Met Met Asn Gln Met Asn Gln Gln Gly Asn
        1135                1140                1145 ttt cct ctc caa gga atg cac cca cga gcc aac atc atg aga ccc cgg    3689
Phe Pro Leu Gln Gly Met His Pro Arg Ala Asn Ile Met Arg Pro Arg
    1150                1155                1160 aca aac acc ccc aag caa ctt aga atg cag ctt cag cag agg ctg cag    3737
Thr Asn Thr Pro Lys Gln Leu Arg Met Gln Leu Gln Gln Arg Leu Gln
1165                1170                1175 ggc cag cag ttt ttg aat cag agc cga cag gca ctt gaa ttg aaa atg    3785
Gly Gln Gln Phe Leu Asn Gln Ser Arg Gln Ala Leu Glu Leu Lys Met
1180                1185                1190                1195 gaa aac cct act gct ggt ggt gct gcg gtg atg agg cct atg atg cag    3833
Glu Asn Pro Thr Ala Gly Gly Ala Ala Val Met Arg Pro Met Met Gln
            1200                1205                1210 ccc cag cag ggt ttt ctt aat gct caa atg gtc gcc caa cgc agc aga    3881
Pro Gln Gln Gly Phe Leu Asn Ala Gln Met Val Ala Gln Arg Ser Arg
        1215                1220                1225 gag ctg cta agt cat cac ttc cga caa cag agg gtg gct atg atg atg    3929
Glu Leu Leu Ser His His Phe Arg Gln Gln Arg Val Ala Met Met Met
    1230                1235                1240
```

| | |
|---|---|
| cag cag cag cag cag cag caa cag cag cag cag cag cag cag cag cag<br>Gln Gln Gln Gln Gln Gln Gln Gln Gln Gln Gln Gln Gln Gln Gln Gln<br>   1245               1250             1255 | 3977 |
| caa cag caa cag caa cag caa cag cag caa cag cag caa acc cag gcc<br>Gln Gln Gln Gln Gln Gln Gln Gln Gln Gln Gln Gln Gln Thr Gln Ala<br>1260               1265             1270             1275 | 4025 |
| ttc agc cca cct cct aat gtg act gct tcc ccc agc atg gat ggg ctt<br>Phe Ser Pro Pro Pro Asn Val Thr Ala Ser Pro Ser Met Asp Gly Leu<br>            1280             1285             1290 | 4073 |
| ttg gca gga ccc aca atg cca caa gct cct ccg caa cag ttt cca tat<br>Leu Ala Gly Pro Thr Met Pro Gln Ala Pro Pro Gln Gln Phe Pro Tyr<br>   1295               1300             1305 | 4121 |
| caa cca aat tat gga atg gga caa caa cca gat cca gcc ttt ggt cga<br>Gln Pro Asn Tyr Gly Met Gly Gln Gln Pro Asp Pro Ala Phe Gly Arg<br>1310               1315             1320 | 4169 |
| gtg tct agt cct ccc aat gca atg atg tcg tca aga atg ggt ccc tcc<br>Val Ser Ser Pro Pro Asn Ala Met Met Ser Ser Arg Met Gly Pro Ser<br>            1325             1330             1335 | 4217 |
| cag aat ccc atg atg caa cac ccg cag gct gca tcc atc tat cag tcc<br>Gln Asn Pro Met Met Gln His Pro Gln Ala Ala Ser Ile Tyr Gln Ser<br>1340               1345             1350             1355 | 4265 |
| tca gaa atg aag ggc tgg cca tca gga aat ttg gcc agg aac agc tcc<br>Ser Glu Met Lys Gly Trp Pro Ser Gly Asn Leu Ala Arg Asn Ser Ser<br>            1360             1365             1370 | 4313 |
| ttt tcc cag cag cag ttt gcc cac cag ggg aat cct gca gtg tat agt<br>Phe Ser Gln Gln Gln Phe Ala His Gln Gly Asn Pro Ala Val Tyr Ser<br>   1375               1380             1385 | 4361 |
| atg gtg cac atg aat ggc agc agt ggt cac atg gga cag atg aac atg<br>Met Val His Met Asn Gly Ser Ser Gly His Met Gly Gln Met Asn Met<br>1390               1395             1400 | 4409 |
| aac ccc atg ccc atg tct ggc atg cct atg ggt cct gat cag aaa tac<br>Asn Pro Met Pro Met Ser Gly Met Pro Met Gly Pro Asp Gln Lys Tyr<br>            1405             1410             1415 | 4457 |
| tgc tga catctctgca ccaggacctc ttaaggaaac cactgtacaa atgacactgc<br>Cys<br>1420 | 4513 |
| actaggatta ttgggaagga atcattgttc caggcatcca tcttggaaga aaggaccagc | 4573 |
| tttgagctcc atcaagggta tttttaagtga tgtcatttga gcaggactgg attttaagcc | 4633 |
| gaagggcaat atctacgtgt ttttccccccc tccttctgct gtgtatcatg gtgttcaaaa | 4693 |
| cagaaatgtt ttttggcatt ccacctccta gggatataat tctggagaca tggagtgtta | 4753 |
| ctgatcataa aacttttgtg tcactttttt ctgccttgct agccaaaatc tcttaaatac | 4813 |
| acgtaggtgg gccagagaac attggaagaa tcaagagaga ttagaatatc tggtttctct | 4873 |
| agttgcagta ttggacaaag agcatagtcc cagccttcag gtgtagtagt tctgtgttga | 4933 |
| ccctttgtcc agtggaattg gtgattctga attgtccttt actaatggtg ttgagttgct | 4993 |
| ctgtccctat tatttgccct aggctttctc ctaatgaagg ttttcatttg ccattcatgt | 5053 |
| cctgtaatac ttcacctcca ggaactgtca tggatgtcca atggctttg cagaaaggaa | 5113 |
| atgagatgac agtatttaat cgcagcagta gcaaactttt cacatgctaa tgtgcagctg | 5173 |
| agtgcacttt atttaaaaag aatggataaa tgcaatattc ttgaggtctt gagggaatag | 5233 |
| tgaaacacat tcctggtttt tgcctacact tacgtgttag acaagaacta tgattttttt | 5293 |
| tttaaagtac tggtgtcacc ctttgcctat atggtagagc aataatgctt ttaaaaata | 5353 |
| aacttctgaa aacccaaggc caggtactgc attctgaatc agaatctcgc agtgtttctg | 5413 |
| tgaatagatt ttttttgtaaa tatgaccttt aagatattgt attatgtaaa atatgtatat | 5473 |

```
accttttttt gtaggtcaca acaactcatt tttacagagt ttgtgaagct aaatatttaa    5533
cattgttgat ttcagtaagc tgtgtggtga ggctaccagt ggaagagaca tcccttgact    5593
tttgtggcct gggggagggg tagtgctcca cagcttttcc ttccccaccc cccagcctta    5653
gatgcctcgc tcttttcaat ctcttaatct aaatgctttt taaagagatt atttgtttag    5713
atgtaggcat tttaatttt taaaaattcc tctaccagaa ctaagcactt tgttaatttg    5773
gggggaaaga atagatatgg ggaaataaac ttaaaaaaaa atcaggaatt taaaaaaacg    5833
agcaatttga agagaatctt ttggatttta agcagtccga aataatagca attcatgggc    5893
tgtgtgtgtg tgtgtatgtg tgtgtgtgtg tgtgtatgtt taattatgtt acctttcat     5953 cccctttagg agcgttttca gattttggtt gctaagacct gaatcccata ttgagatctc    6013
gagtagaatc cttggtgtgg tttctggtgt ctgctcagct gtcccctcat tctactaatg    6073
tgatgctttc attatgtccc tgtggattag aatagtgtca gttatttctt aagtaactca    6133
gtacccagaa cagccagttt tactgtgatt cagagccaca gtctaactga gcacctttta    6193
aacccctccc tcttctgccc cctaccactt ttctgctgtt gcctctcttt gacacctgtt    6253
ttagtcagtt gggaggaagg gaaaaatcaa gtttaattcc ctttatctgg gttaattcat    6313
ttggttcaaa tagttgacgg aattgggttt ctgaatgtct gtgaatttca gaggtctctg    6373
ctagccttgg tatcatttc tagcaataac tgagagccag ttaattttaa gaatttcaca     6433
catttagcca atcttctag atgtctctga aggtaagatc atttaatatc tttgatatgc     6493
ttacgagtaa gtgaatcctg attatttcca gacccaccac cagagtggat cttattttca    6553
aagcagtata gacaattatg agtttgccct ctttccccta ccaagttcaa aatatatcta    6613
agaaagattg taaatccgaa aacttccatt gtagtggcct gtgcttttca gatagtatac    6673
tctcctgttt ggagacagag gaagaaccag gtcagtctgt ctctttttca gctcaattgt    6733
atctgaccct tctttaagtt atgtgtgtgg ggagaaatag aatggtgctc ttatctttct    6793
tgactttaaa aaaattatta aaacaaaaa aaaaaaaaa aa                         6835
```

<210> SEQ ID NO 2
<211> LENGTH: 186
<212> TYPE: PRT
<213> ORGANISM: Homo sapiens

<400> SEQUENCE: 2

```
Leu Leu Gln Ala Leu Asp Gly Phe Leu Phe Val Val Asn Arg Asp Gly
  1               5                  10                  15

Asn Ile Val Phe Val Ser Glu Asn Val Thr Gln Tyr Leu Gln Tyr Lys
             20                  25                  30

Gln Glu Asp Leu Val Asn Thr Ser Val Tyr Asn Ile Leu His Glu Glu
         35                  40                  45

Asp Arg Lys Asp Phe Leu Lys Asn Leu Pro Lys Ser Thr Val Asn Gly
     50                  55                  60

Val Ser Trp Thr Asn Glu Thr Gln Arg Gln Lys Ser His Thr Phe Asn
 65                  70                  75                  80

Cys Arg Met Leu Met Lys Thr Pro His Asp Ile Leu Glu Asp Ile Asn
                 85                  90                  95

Ala Ser Pro Glu Met Arg Gln Arg Tyr Glu Thr Met Gln Cys Phe Ala
            100                 105                 110

Leu Ser Gln Pro Arg Ala Met Met Glu Glu Gly Glu Asp Leu Gln Ser
        115                 120                 125
```

```
Cys Met Ile Cys Val Ala Arg Arg Ile Thr Thr Gly Glu Arg Thr Phe
    130                 135                 140

Pro Ser Asn Pro Glu Ser Phe Ile Thr Arg His Asp Leu Ser Gly Lys
145                 150                 155                 160

Val Val Asn Ile Asp Thr Asn Ser Leu Arg Ser Ser Met Arg Pro Gly
                165                 170                 175

Phe Glu Asp Ile Ile Arg Arg Cys Ile Gln
                180                 185

<210> SEQ ID NO 3
<211> LENGTH: 73
<212> TYPE: PRT
<213> ORGANISM: Homo sapiens

<400> SEQUENCE: 3

Arg Lys Arg Lys Leu Pro Cys Asp Thr Pro Gly Gln Gly Leu Thr Cys
1               5                   10                  15

Ser Gly Glu Lys Arg Arg Glu Gln Glu Ser Lys Tyr Ile Glu Glu
                20                  25                  30

Leu Ala Glu Leu Ile Ser Ala Asn Leu Ser Asp Ile Asp Asn Phe Asn
            35                  40                  45

Val Lys Pro Asp Lys Cys Ala Ile Leu Lys Glu Thr Val Arg Gln Ile
        50                  55                  60

Arg Gln Ile Lys Glu Gln Gly Lys Thr
65                  70

<210> SEQ ID NO 4
<211> LENGTH: 1420
<212> TYPE: PRT
<213> ORGANISM: Homo sapiens

<400> SEQUENCE: 4

Met Ser Gly Leu Gly Glu Asn Leu Asp Pro Leu Ala Ser Asp Ser Arg
1               5                   10                  15

Lys Arg Lys Leu Pro Cys Asp Thr Pro Gly Gln Gly Leu Thr Cys Ser
                20                  25                  30

Gly Glu Lys Arg Arg Glu Gln Glu Ser Lys Tyr Ile Glu Glu Leu
            35                  40                  45

Ala Glu Leu Ile Ser Ala Asn Leu Ser Asp Ile Asp Asn Phe Asn Val
        50                  55                  60

Lys Pro Asp Lys Cys Ala Ile Leu Lys Glu Thr Val Arg Gln Ile Arg
65                  70                  75                  80

Gln Ile Lys Glu Gln Gly Lys Thr Ile Ser Asn Asp Asp Val Gln
                85                  90                  95

Lys Ala Asp Val Ser Ser Thr Gly Gln Gly Val Ile Asp Lys Asp Ser
                100                 105                 110

Leu Gly Pro Leu Leu Leu Gln Ala Leu Asp Gly Phe Leu Phe Val Val
            115                 120                 125

Asn Arg Asp Gly Asn Ile Val Phe Val Ser Glu Asn Val Thr Gln Tyr
        130                 135                 140

Leu Gln Tyr Lys Gln Glu Asp Leu Val Asn Thr Ser Val Tyr Asn Ile
145                 150                 155                 160

Leu His Glu Glu Asp Arg Lys Asp Phe Leu Lys Asn Leu Pro Lys Ser
                165                 170                 175

Thr Val Asn Gly Val Ser Trp Thr Asn Glu Thr Gln Arg Gln Lys Ser
                180                 185                 190
```

```
His Thr Phe Asn Cys Arg Met Leu Met Lys Thr Pro His Asp Ile Leu
        195                 200                 205

Glu Asp Ile Asn Ala Ser Pro Glu Met Arg Gln Arg Tyr Glu Thr Met
210                 215                 220

Gln Cys Phe Ala Leu Ser Gln Pro Arg Ala Met Met Glu Glu Gly Glu
225                 230                 235                 240

Asp Leu Gln Ser Cys Met Ile Cys Val Ala Arg Arg Ile Thr Thr Gly
                245                 250                 255

Glu Arg Thr Phe Pro Ser Asn Pro Glu Ser Phe Ile Thr Arg His Asp
            260                 265                 270

Leu Ser Gly Lys Val Val Asn Ile Asp Thr Asn Ser Leu Arg Ser Ser
        275                 280                 285

Met Arg Pro Gly Phe Glu Asp Ile Ile Arg Arg Cys Ile Gln Arg Phe
    290                 295                 300

Phe Ser Leu Asn Asp Gly Gln Ser Trp Ser Gln Lys Arg His Tyr Gln
305                 310                 315                 320

Glu Ala Tyr Leu Asn Gly His Ala Glu Thr Pro Val Tyr Arg Phe Ser
                325                 330                 335

Leu Ala Asp Gly Thr Ile Val Thr Ala Gln Thr Lys Ser Lys Leu Phe
            340                 345                 350

Arg Asn Pro Val Thr Asn Asp Arg His Gly Phe Val Ser Thr His Phe
        355                 360                 365

Leu Gln Arg Glu Gln Asn Gly Tyr Arg Pro Asn Pro Asn Pro Val Gly
    370                 375                 380

Gln Gly Ile Arg Pro Pro Met Ala Gly Cys Asn Ser Ser Val Gly Gly
385                 390                 395                 400

Met Ser Met Ser Pro Asn Gln Gly Leu Gln Met Pro Ser Ser Arg Ala
                405                 410                 415

Tyr Gly Leu Ala Asp Pro Ser Thr Thr Gly Gln Met Ser Gly Ala Arg
            420                 425                 430

Tyr Gly Gly Ser Ser Asn Ile Ala Ser Leu Thr Pro Gly Pro Gly Met
        435                 440                 445

Gln Ser Pro Ser Ser Tyr Gln Asn Asn Asn Tyr Gly Leu Asn Met Ser
    450                 455                 460

Ser Pro Pro His Gly Ser Pro Gly Leu Ala Pro Asn Gln Gln Asn Ile
465                 470                 475                 480

Met Ile Ser Pro Arg Asn Arg Gly Ser Pro Lys Ile Ala Ser His Gln
                485                 490                 495

Phe Ser Pro Val Ala Gly Val His Ser Pro Met Ala Ser Ser Gly Asn
            500                 505                 510

Thr Gly Asn His Ser Phe Ser Ser Ser Leu Ser Ala Leu Gln Ala
        515                 520                 525

Ile Ser Glu Gly Val Gly Thr Ser Leu Leu Ser Thr Leu Ser Ser Pro
    530                 535                 540

Gly Pro Lys Leu Asp Asn Ser Pro Asn Met Asn Ile Thr Gln Pro Ser
545                 550                 555                 560

Lys Val Ser Asn Gln Asp Ser Lys Ser Pro Leu Gly Phe Tyr Cys Asp
                565                 570                 575

Gln Asn Pro Val Glu Ser Ser Met Cys Gln Ser Asn Ser Arg Asp His
            580                 585                 590

Leu Ser Asp Lys Glu Ser Lys Glu Ser Val Glu Gly Ala Glu Asn
        595                 600                 605

Gln Arg Gly Pro Leu Glu Ser Lys Gly His Lys Lys Leu Leu Gln Leu
```

```
         610                 615                 620
Leu Thr Cys Ser Ser Asp Asp Arg Gly His Ser Ser Leu Thr Asn Ser
625                 630                 635                 640

Pro Leu Asp Ser Ser Cys Lys Glu Ser Ser Val Ser Val Thr Ser Pro
                    645                 650                 655

Ser Gly Val Ser Ser Ser Thr Ser Gly Gly Val Ser Ser Thr Ser Asn
                660                 665                 670

Met His Gly Ser Leu Leu Gln Glu Lys His Arg Ile Leu His Lys Leu
            675                 680                 685

Leu Gln Asn Gly Asn Ser Pro Ala Glu Val Ala Lys Ile Thr Ala Glu
690                 695                 700

Ala Thr Gly Lys Asp Thr Ser Ile Thr Ser Cys Gly Asp Gly Asn
705                 710                 715                 720

Val Val Lys Gln Glu Gln Leu Ser Pro Lys Lys Glu Asn Asn Ala
                725                 730                 735

Leu Leu Arg Tyr Leu Leu Asp Arg Asp Asp Pro Ser Asp Ala Leu Ser
                740                 745                 750

Lys Glu Leu Gln Pro Gln Val Glu Gly Val Asp Asn Lys Met Ser Gln
            755                 760                 765

Cys Thr Ser Ser Thr Ile Pro Ser Ser Gln Glu Lys Asp Pro Lys
770                 775                 780

Ile Lys Thr Glu Thr Ser Glu Glu Gly Ser Gly Asp Leu Asp Asn Leu
785                 790                 795                 800

Asp Ala Ile Leu Gly Asp Leu Thr Ser Ser Asp Phe Tyr Asn Asn Ser
                805                 810                 815

Ile Ser Ser Asn Gly Ser His Leu Gly Thr Lys Gln Gln Val Phe Gln
                820                 825                 830

Gly Thr Asn Ser Leu Gly Leu Lys Ser Ser Gln Ser Val Gln Ser Ile
            835                 840                 845

Arg Pro Pro Tyr Asn Arg Ala Val Ser Leu Asp Ser Pro Val Ser Val
850                 855                 860

Gly Ser Ser Pro Pro Val Lys Asn Ile Ser Ala Phe Pro Met Leu Pro
865                 870                 875                 880

Lys Gln Pro Met Leu Gly Gly Asn Pro Arg Met Met Asp Ser Gln Glu
                885                 890                 895

Asn Tyr Gly Ser Ser Met Gly Gly Pro Asn Arg Asn Val Thr Val Thr
            900                 905                 910

Gln Thr Pro Ser Ser Gly Asp Trp Gly Leu Pro Asn Ser Lys Ala Gly
            915                 920                 925

Arg Met Glu Pro Met Asn Ser Asn Ser Met Gly Arg Pro Gly Gly Asp
930                 935                 940

Tyr Asn Thr Ser Leu Pro Arg Pro Ala Leu Gly Gly Ser Ile Pro Thr
945                 950                 955                 960

Leu Pro Leu Arg Ser Asn Ser Ile Pro Gly Ala Arg Pro Val Leu Gln
                965                 970                 975

Gln Gln Gln Gln Met Leu Gln Met Arg Pro Gly Glu Ile Pro Met Gly
                980                 985                 990

Met Gly Ala Asn Pro Tyr Gly Gln Ala Ala Ala Ser Asn Gln Leu Gly
            995                 1000                1005

Ser Trp Pro Asp Gly Met Leu Ser Met Glu Gln Val Ser His Gly Thr
            1010                1015                1020

Gln Asn Arg Pro Leu Leu Arg Asn Ser Leu Asp Asp Leu Val Gly Pro
1025                1030                1035                1040
```

```
Pro Ser Asn Leu Glu Gly Gln Ser Asp Glu Arg Ala Leu Leu Asp Gln
            1045                1050                1055

Leu His Thr Leu Leu Ser Asn Thr Asp Ala Thr Gly Leu Glu Glu Ile
        1060                1065                1070

Asp Arg Ala Leu Gly Ile Pro Glu Leu Val Asn Gln Gly Gln Ala Leu
        1075                1080                1085

Glu Pro Lys Gln Asp Ala Phe Gln Gly Gln Glu Ala Ala Val Met Met
    1090                1095                1100

Asp Gln Lys Ala Gly Leu Tyr Gly Gln Thr Tyr Pro Ala Gln Gly Pro
1105                1110                1115                1120

Pro Met Gln Gly Gly Phe His Leu Gln Gly Gln Ser Pro Ser Phe Asn
            1125                1130                1135

Ser Met Met Asn Gln Met Asn Gln Gln Gly Asn Phe Pro Leu Gln Gly
        1140                1145                1150

Met His Pro Arg Ala Asn Ile Met Arg Pro Arg Thr Asn Thr Pro Lys
        1155                1160                1165

Gln Leu Arg Met Gln Leu Gln Gln Arg Leu Gly Gln Gln Phe Leu
    1170                1175                1180

Asn Gln Ser Arg Gln Ala Leu Glu Leu Lys Met Glu Asn Pro Thr Ala
1185                1190                1195                1200

Gly Gly Ala Ala Val Met Arg Pro Met Met Gln Pro Gln Gln Gly Phe
            1205                1210                1215

Leu Asn Ala Gln Met Val Ala Gln Arg Ser Arg Glu Leu Leu Ser His
        1220                1225                1230

His Phe Arg Gln Gln Arg Val Ala Met Met Met Gln Gln Gln Gln Gln
        1235                1240                1245

Gln Gln Gln Gln Gln Gln Gln Gln Gln Gln Gln Gln Gln Gln Gln Gln
    1250                1255                1260

Gln Gln Gln Gln Gln Gln Gln Thr Gln Ala Phe Ser Pro Pro Pro
1265                1270                1275                1280

Asn Val Thr Ala Ser Pro Ser Met Asp Gly Leu Leu Ala Gly Pro Thr
            1285                1290                1295

Met Pro Gln Ala Pro Pro Gln Gln Phe Pro Tyr Gln Pro Asn Tyr Gly
        1300                1305                1310

Met Gly Gln Gln Pro Asp Pro Ala Phe Gly Arg Val Ser Ser Pro Pro
    1315                1320                1325

Asn Ala Met Met Ser Ser Arg Met Gly Pro Ser Gln Asn Pro Met Met
1330                1335                1340

Gln His Pro Gln Ala Ala Ser Ile Tyr Gln Ser Ser Glu Met Lys Gly
1345                1350                1355                1360

Trp Pro Ser Gly Asn Leu Ala Arg Asn Ser Ser Phe Ser Gln Gln Gln
            1365                1370                1375

Phe Ala His Gln Gly Asn Pro Ala Val Tyr Ser Met Val His Met Asn
        1380                1385                1390

Gly Ser Ser Gly His Met Gly Gln Met Asn Met Asn Pro Met Pro Met
    1395                1400                1405

Ser Gly Met Pro Met Gly Pro Asp Gln Lys Tyr Cys
    1410                1415                1420

<210> SEQ ID NO 5
<211> LENGTH: 22
<212> TYPE: DNA
<213> ORGANISM: Artificial Sequence
<220> FEATURE:
```

-continued

```
<223> OTHER INFORMATION: Description of Artificial Sequence:PRIMER N8F1

<400> SEQUENCE: 5
tcatcacttc cgacaacaga gg                                              22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: forward
      primer designed from the 5' sequence of pCMVSPORT-B11, PM-U2

<400> SEQUENCE: 6
ccagaaacgt cactatcaag                                                 20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: reverse
      primer designed from the 5' sequence of pCMVSPORT-B11, PM-U2

<400> SEQUENCE: 7
ttactggaac ccccatacc                                                  19

<210> SEQ ID NO 8
<211> LENGTH: 951
<212> TYPE: PRT
<213> ORGANISM: Homo sapiens

<400> SEQUENCE: 8
```

Cys Ile Gln Arg Phe Phe Ser Leu Asn Asp Gly Gln Ser Trp Ser Gln
  1               5                  10                  15

Lys Arg His Tyr Gln Glu Ala Tyr Leu Asn Gly His Ala Glu Thr Pro
                 20                  25                  30

Val Tyr Arg Phe Ser Leu Ala Asp Gly Thr Ile Val Thr Ala Gln Thr
             35                  40                  45

Lys Ser Lys Leu Phe Arg Asn Pro Val Thr Asn Asp Arg His Gly Phe
 50                  55                  60

Val Ser Thr His Phe Leu Gln Arg Glu Gln Asn Gly Tyr Arg Pro Asn
 65                  70                  75                  80

Pro Asn Pro Val Gly Gln Gly Ile Arg Pro Met Ala Gly Cys Asn
                 85                  90                  95

Ser Ser Val Gly Gly Met Ser Met Ser Pro Asn Gln Gly Leu Gln Met
                100                 105                 110

Pro Ser Ser Arg Ala Tyr Gly Leu Ala Asp Pro Ser Thr Thr Gly Gln
            115                 120                 125

Met Ser Gly Ala Arg Tyr Gly Gly Ser Ser Asn Ile Ala Ser Leu Thr
130                 135                 140

Pro Gly Pro Gly Met Gln Ser Pro Ser Tyr Gln Asn Asn Asn Tyr
145                 150                 155                 160

Gly Leu Asn Met Ser Ser Pro Pro His Gly Ser Pro Gly Leu Ala Pro
                165                 170                 175

Asn Gln Gln Asn Ile Met Ile Ser Pro Arg Asn Arg Gly Ser Pro Lys
            180                 185                 190

Ile Ala Ser His Gln Phe Ser Pro Val Ala Gly Val His Ser Pro Met
        195                 200                 205

-continued

```
Ala Ser Ser Gly Asn Thr Gly Asn His Ser Phe Ser Ser Ser Ser Leu
    210                 215                 220
Ser Ala Leu Gln Ala Ile Ser Glu Gly Val Gly Thr Ser Leu Leu Ser
225                 230                 235                 240
Thr Leu Ser Ser Pro Gly Pro Lys Leu Asp Asn Ser Pro Asn Met Asn
                245                 250                 255
Ile Thr Gln Pro Ser Lys Val Ser Asn Gln Asp Ser Lys Ser Pro Leu
            260                 265                 270
Gly Phe Tyr Cys Asp Gln Asn Pro Val Glu Ser Ser Met Cys Gln Ser
        275                 280                 285
Asn Ser Arg Asp His Leu Ser Asp Lys Glu Ser Lys Glu Ser Ser Val
    290                 295                 300
Glu Gly Ala Glu Asn Gln Arg Gly Pro Leu Ser Lys Gly His Lys
305                 310                 315                 320
Lys Leu Leu Gln Leu Leu Thr Cys Ser Ser Asp Asp Arg Gly His Ser
                325                 330                 335
Ser Leu Thr Asn Ser Pro Leu Asp Ser Ser Cys Lys Glu Ser Ser Val
            340                 345                 350
Ser Val Thr Ser Pro Ser Gly Val Ser Ser Ser Thr Ser Gly Gly Val
        355                 360                 365
Ser Ser Thr Ser Asn Met His Gly Ser Leu Leu Gln Glu Lys His Arg
    370                 375                 380
Ile Leu His Lys Leu Leu Gln Asn Gly Asn Ser Pro Ala Glu Val Ala
385                 390                 395                 400
Lys Ile Thr Ala Glu Ala Thr Gly Lys Asp Thr Ser Ser Ile Thr Ser
                405                 410                 415
Cys Gly Asp Gly Asn Val Val Lys Gln Glu Gln Leu Ser Pro Lys Lys
            420                 425                 430
Lys Glu Asn Asn Ala Leu Leu Arg Tyr Leu Leu Asp Arg Asp Asp Pro
        435                 440                 445
Ser Asp Ala Leu Ser Lys Glu Leu Gln Pro Gln Val Glu Gly Val Asp
    450                 455                 460
Asn Lys Met Ser Gln Cys Thr Ser Ser Thr Ile Pro Ser Ser Ser Gln
465                 470                 475                 480
Glu Lys Asp Pro Lys Ile Lys Thr Glu Thr Ser Glu Glu Gly Ser Gly
                485                 490                 495
Asp Leu Asp Asn Leu Asp Ala Ile Leu Gly Asp Leu Thr Ser Ser Asp
            500                 505                 510
Phe Tyr Asn Asn Ser Ile Ser Ser Asn Gly Ser His Leu Gly Thr Lys
        515                 520                 525
Gln Gln Val Phe Gln Gly Thr Asn Ser Leu Gly Leu Lys Ser Ser Gln
    530                 535                 540
Ser Val Gln Ser Ile Arg Pro Pro Tyr Asn Arg Ala Val Ser Leu Asp
545                 550                 555                 560
Ser Pro Val Ser Val Gly Ser Ser Pro Val Lys Asn Ile Ser Ala
                565                 570                 575
Phe Pro Met Leu Pro Lys Gln Pro Met Leu Gly Gly Asn Pro Arg Met
            580                 585                 590
Met Asp Ser Gln Glu Asn Tyr Gly Ser Ser Met Gly Gly Pro Asn Arg
        595                 600                 605
Asn Val Thr Val Thr Gln Thr Pro Ser Ser Gly Asp Trp Gly Leu Pro
    610                 615                 620
Asn Ser Lys Ala Gly Arg Met Glu Pro Met Asn Ser Asn Ser Met Gly
```

```
625                 630                 635                 640

Arg Pro Gly Gly Asp Tyr Asn Thr Ser Leu Pro Pro Ala Leu Gly
                645                 650                 655

Gly Ser Ile Pro Thr Leu Pro Leu Arg Ser Asn Ser Ile Pro Gly Ala
                660                 665                 670

Arg Pro Val Leu Gln Gln Gln Gln Met Leu Gln Met Arg Pro Gly
                675                 680                 685

Glu Ile Pro Met Gly Met Gly Ala Asn Pro Tyr Gly Gln Ala Ala Ala
                690                 695                 700

Ser Asn Gln Leu Gly Ser Trp Pro Asp Gly Met Leu Ser Met Glu Gln
705                 710                 715                 720

Val Ser His Gly Thr Gln Asn Arg Pro Leu Leu Arg Asn Ser Leu Asp
                725                 730                 735

Asp Leu Val Gly Pro Pro Ser Asn Leu Glu Gly Gln Ser Asp Glu Arg
                740                 745                 750

Ala Leu Leu Asp Gln Leu His Thr Leu Leu Ser Asn Thr Asp Ala Thr
                755                 760                 765

Gly Leu Glu Glu Ile Asp Arg Ala Leu Gly Ile Pro Glu Leu Val Asn
                770                 775                 780

Gln Gly Gln Ala Leu Glu Pro Lys Gln Asp Ala Phe Gln Gly Gln Glu
785                 790                 795                 800

Ala Ala Val Met Met Asp Gln Lys Ala Gly Leu Tyr Gly Gln Thr Tyr
                805                 810                 815

Pro Ala Gln Gly Pro Pro Met Gln Gly Gly Phe His Leu Gln Gly Gln
                820                 825                 830

Ser Pro Ser Phe Asn Ser Met Met Asn Gln Met Asn Gln Gln Gly Asn
                835                 840                 845

Phe Pro Leu Gln Gly Met His Pro Arg Ala Asn Ile Met Arg Pro Arg
850                 855                 860

Thr Asn Thr Pro Lys Gln Leu Arg Met Gln Leu Gln Arg Leu Gln
865                 870                 875                 880

Gly Gln Gln Phe Leu Asn Gln Ser Arg Gln Ala Leu Glu Leu Lys Met
                885                 890                 895

Glu Asn Pro Thr Ala Gly Gly Ala Ala Val Met Arg Pro Met Met Gln
                900                 905                 910

Pro Gln Gln Gly Phe Leu Asn Ala Gln Met Val Ala Gln Arg Ser Arg
                915                 920                 925

Glu Leu Leu Ser His His Phe Arg Gln Gln Arg Val Ala Met Met Met
    930                 935                 940

Gln Gln Gln Gln Gln Gln Gln
945                 950

<210> SEQ ID NO 9
<211> LENGTH: 4621
<212> TYPE: DNA
<213> ORGANISM: Mus musculus
<220> FEATURE:
<221> NAME/KEY: CDS
<222> LOCATION: (110)..(4318)

<400> SEQUENCE: 9
ggcggcgaac ggatcaaaag aatttgctga acagtggact ccgagatcgg taaaacgaac      60
tcttccctgc ccttcctgaa cagctgtcag ttgctgatct gtgatcagg atg agt gga    118
                                                       Met Ser Gly
                                                         1
```

-continued

| | | |
|---|---|---|
| cta ggc gaa agc tct ttg gat ccg ctg gcc gct gag tct cgg aaa cgc<br>Leu Gly Glu Ser Ser Leu Asp Pro Leu Ala Ala Glu Ser Arg Lys Arg<br>5                   10                     15 | 166 |
| aaa ctg ccc tgt gat gcc cca gga cag ggg ctt gtc tac agt ggt gag<br>Lys Leu Pro Cys Asp Ala Pro Gly Gln Gly Leu Val Tyr Ser Gly Glu<br>20                   25                     30                     35 | 214 |
| aag tgg cga cgg gag cag gag agc aag tac ata gag gag ctg gca gag<br>Lys Trp Arg Arg Glu Gln Glu Ser Lys Tyr Ile Glu Glu Leu Ala Glu<br>40                   45                     50 | 262 |
| ctc atc tct gca aat ctc agc gac atc gac aac ttc aat gtc aag cca<br>Leu Ile Ser Ala Asn Leu Ser Asp Ile Asp Asn Phe Asn Val Lys Pro<br>55                   60                     65 | 310 |
| gat aaa tgt gcc atc cta aag gag aca gtg aga cag ata cgg caa ata<br>Asp Lys Cys Ala Ile Leu Lys Glu Thr Val Arg Gln Ile Arg Gln Ile<br>70                   75                     80 | 358 |
| aaa gaa caa gga aaa act att tcc agt gat gat gat gtt caa aaa gct<br>Lys Glu Gln Gly Lys Thr Ile Ser Ser Asp Asp Asp Val Gln Lys Ala<br>85                   90                     95 | 406 |
| gat gtg tct tct aca ggg cag gga gtc att gat aaa gac tct tta gga<br>Asp Val Ser Ser Thr Gly Gln Gly Val Ile Asp Lys Asp Ser Leu Gly<br>100                 105                110               115 | 454 |
| ccg ctt tta cta cag gca ctg gat ggt ttc ctg ttt gtg gtg aat cga<br>Pro Leu Leu Leu Gln Ala Leu Asp Gly Phe Leu Phe Val Val Asn Arg<br>120                         125                    130 | 502 |
| gat gga aac att gta ttc gtg tca gaa aat gtc aca cag tat ctg cag<br>Asp Gly Asn Ile Val Phe Val Ser Glu Asn Val Thr Gln Tyr Leu Gln<br>135                  140                   145 | 550 |
| tac aag cag gag gac ctg gtt aac aca agt gtc tac agc atc tta cat<br>Tyr Lys Gln Glu Asp Leu Val Asn Thr Ser Val Tyr Ser Ile Leu His<br>150                   155                  160 | 598 |
| gag caa gac cgg aag gat ttt ctt aaa cac tta cca aaa tcc aca gtt<br>Glu Gln Asp Arg Lys Asp Phe Leu Lys His Leu Pro Lys Ser Thr Val<br>165                  170                175 | 646 |
| aat gga gtt tct tgg act aat gag aac cag aga caa aaa agc cat aca<br>Asn Gly Val Ser Trp Thr Asn Glu Asn Gln Arg Gln Lys Ser His Thr<br>180                   185                190              195 | 694 |
| ttt aat tgt cgt atg ttg atg aaa aca cac gac att ttg gaa gac gtg<br>Phe Asn Cys Arg Met Leu Met Lys Thr His Asp Ile Leu Glu Asp Val<br>200                   205                210 | 742 |
| aat gcc agt ccc gaa aca cgc cag aga tat gaa aca atg cag tgc ttt<br>Asn Ala Ser Pro Glu Thr Arg Gln Arg Tyr Glu Thr Met Gln Cys Phe<br>215                   220                225 | 790 |
| gcc ctg tct cag cct cgc gct atg ctg gaa gaa gga gaa gac ttg cag<br>Ala Leu Ser Gln Pro Arg Ala Met Leu Glu Glu Gly Glu Asp Leu Gln<br>230                   235                240 | 838 |
| tgc tgt atg atc tgc gtg gct cgc cgc gtg act gcg cca ttc cca tcc<br>Cys Cys Met Ile Cys Val Ala Arg Arg Val Thr Ala Pro Phe Pro Ser<br>245                   250                255 | 886 |
| agt cct gag agc ttt att acc aga cat gac ctt tcc gga aag gtt gtc<br>Ser Pro Glu Ser Phe Ile Thr Arg His Asp Leu Ser Gly Lys Val Val<br>260                   265                270               275 | 934 |
| aat ata gat aca aac tca ctt aga tct tcc atg agg cct ggc ttt gaa<br>Asn Ile Asp Thr Asn Ser Leu Arg Ser Ser Met Arg Pro Gly Phe Glu<br>280                   285                290 | 982 |
| gac ata atc cga aga tgt atc cag agg ttc ttc agt ctg aat gat ggg<br>Asp Ile Ile Arg Arg Cys Ile Gln Arg Phe Phe Ser Leu Asn Asp Gly<br>295                   300                305 | 1030 |
| cag tca tgg tcc cag aag cgt cac tat caa gaa gct tat gtt cat ggc<br>Gln Ser Trp Ser Gln Lys Arg His Tyr Gln Glu Ala Tyr Val His Gly<br>310                   315                320 | 1078 |

-continued

```
cac gca gag acc ccc gtg tat cgt ttc tcc ttg gct gat gga act att    1126
His Ala Glu Thr Pro Val Tyr Arg Phe Ser Leu Ala Asp Gly Thr Ile
    325                 330                 335 gtg agt gcg cag aca aaa agc aaa ctc ttc cgc aat cct gta acg aat    1174
Val Ser Ala Gln Thr Lys Ser Lys Leu Phe Arg Asn Pro Val Thr Asn
340                 345                 350                 355 gat cgt cac ggc ttc atc tcg acc cac ttt ctt cag aga gaa cag aat    1222
Asp Arg His Gly Phe Ile Ser Thr His Phe Leu Gln Arg Glu Gln Asn
                360                 365                 370 gga tac aga cca aac cca aat ccc gca gga caa ggc atc cga cct cct    1270
Gly Tyr Arg Pro Asn Pro Asn Pro Ala Gly Gln Gly Ile Arg Pro Pro
            375                 380                 385 gca gca ggg tgt ggc gtg agc atg tct cca aat cag aat gta cag atg    1318
Ala Ala Gly Cys Gly Val Ser Met Ser Pro Asn Gln Asn Val Gln Met
        390                 395                 400 atg ggc agc cgg acc tat ggc gtg cca gac ccc agc aac aca ggg cag    1366
Met Gly Ser Arg Thr Tyr Gly Val Pro Asp Pro Ser Asn Thr Gly Gln
    405                 410                 415 atg ggt gga gct agg tac ggg gct tct agt agc gta gcc tca ctg acg    1414
Met Gly Gly Ala Arg Tyr Gly Ala Ser Ser Ser Val Ala Ser Leu Thr
420                 425                 430                 435 cca gga caa agc cta cag tcg cca tct tcc tat cag aac agc agc tat    1462
Pro Gly Gln Ser Leu Gln Ser Pro Ser Ser Tyr Gln Asn Ser Ser Tyr
                440                 445                 450 ggg ctc agc atg agc agt ccc ccc cac ggc agt cct ggt ctt ggt ccc    1510
Gly Leu Ser Met Ser Ser Pro Pro His Gly Ser Pro Gly Leu Gly Pro
            455                 460                 465 aac cag cag aac atc atg att tcc cct cgg aat cgt ggc agc cca aag    1558
Asn Gln Gln Asn Ile Met Ile Ser Pro Arg Asn Arg Gly Ser Pro Lys
        470                 475                 480 atg gcc tcc cac cag ttc tct cct gct gca ggt gca cac tca ccc atg    1606
Met Ala Ser His Gln Phe Ser Pro Ala Ala Gly Ala His Ser Pro Met
    485                 490                 495 gga cct tct ggc aac aca ggg agc cac agc ttt tct agc agc tcc ctc    1654
Gly Pro Ser Gly Asn Thr Gly Ser His Ser Phe Ser Ser Ser Ser Leu
500                 505                 510                 515 agt gcc ttg caa gcc atc agt gaa ggc gtg ggg acc tct ctt tta tct    1702
Ser Ala Leu Gln Ala Ile Ser Glu Gly Val Gly Thr Ser Leu Leu Ser
                520                 525                 530 act ctg tcc tca cca ggc ccc aaa ctg gat aat tct ccc aat atg aat    1750
Thr Leu Ser Ser Pro Gly Pro Lys Leu Asp Asn Ser Pro Asn Met Asn
            535                 540                 545 ata agc cag cca agt aaa gtg agt ggt cag gac tct aag agc ccc cta    1798
Ile Ser Gln Pro Ser Lys Val Ser Gly Gln Asp Ser Lys Ser Pro Leu
        550                 555                 560 ggc tta tac tgt gaa cag aat cca gtg gag agt tca gtg tgt cag tca    1846
Gly Leu Tyr Cys Glu Gln Asn Pro Val Glu Ser Ser Val Cys Gln Ser
    565                 570                 575 aac agc aga gat cac cca agt gaa aaa gaa agc aag gag agc agt ggg    1894
Asn Ser Arg Asp His Pro Ser Glu Lys Glu Ser Lys Glu Ser Ser Gly
580                 585                 590                 595 gag gtg tca gag acg ccc agg gga cct ctg gaa agc aaa ggc cac aag    1942
Glu Val Ser Glu Thr Pro Arg Gly Pro Leu Glu Ser Lys Gly His Lys
                600                 605                 610 aaa ctg ctg cag tta ctc acg tgc tcc tcc gac gac cga ggc cat tcc    1990
Lys Leu Leu Gln Leu Leu Thr Cys Ser Ser Asp Asp Arg Gly His Ser
            615                 620                 625 tcc ttg acc aac tct ccc ctg gat cca aac tgc aaa gac tct tcc gtt    2038
Ser Leu Thr Asn Ser Pro Leu Asp Pro Asn Cys Lys Asp Ser Ser Val
```

-continued

|  |  | 630 |  |  |  | 635 |  |  |  | 640 |  |  |  |  |  |
|---|---|---|---|---|---|---|---|---|---|---|---|---|---|---|---|
| agt | gtc | acc | agc | ccc | tct | gga | gtg | tcc | tcc | tca | aca | tca | ggg | aca | gtg | 2086 |
| Ser | Val | Thr | Ser | Pro | Ser | Gly | Val | Ser | Ser | Ser | Thr | Ser | Gly | Thr | Val |  |
|  | 645 |  |  |  |  | 650 |  |  |  |  | 655 |  |  |  |  |  |

| tct | tcc | acc | tcc | aat | gtg | cat | ggg | tct | ctg | ttg | caa | gag | aaa | cac | cgg | 2134 |
| Ser | Ser | Thr | Ser | Asn | Val | His | Gly | Ser | Leu | Leu | Gln | Glu | Lys | His | Arg |  |
| 660 |  |  |  |  | 665 |  |  |  |  | 670 |  |  |  |  | 675 |  |

| att | ttg | cac | aag | ttg | ctg | cag | aat | ggc | aac | tcc | cca | gcg | gag | gtc | gcc | 2182 |
| Ile | Leu | His | Lys | Leu | Leu | Gln | Asn | Gly | Asn | Ser | Pro | Ala | Glu | Val | Ala |  |
|  |  |  |  |  | 680 |  |  |  |  | 685 |  |  |  |  | 690 |  |

| aag | atc | act | gca | gag | gcc | act | ggg | aag | gac | acg | agc | agc | act | gct | tcc | 2230 |
| Lys | Ile | Thr | Ala | Glu | Ala | Thr | Gly | Lys | Asp | Thr | Ser | Ser | Thr | Ala | Ser |  |
|  |  |  |  | 695 |  |  |  |  | 700 |  |  |  |  | 705 |  |  |

| tgt | gga | gag | ggg | aca | acc | agg | cag | gag | cag | ctg | agt | cct | aag | aag | aag | 2278 |
| Cys | Gly | Glu | Gly | Thr | Thr | Arg | Gln | Glu | Gln | Leu | Ser | Pro | Lys | Lys | Lys |  |
|  |  |  | 710 |  |  |  |  | 715 |  |  |  |  | 720 |  |  |  |

| gag | aat | aat | gct | ctg | ctt | aga | tac | ctg | ctg | gac | agg | gat | gac | ccc | agt | 2326 |
| Glu | Asn | Asn | Ala | Leu | Leu | Arg | Tyr | Leu | Leu | Asp | Arg | Asp | Asp | Pro | Ser |  |
|  | 725 |  |  |  |  | 730 |  |  |  |  | 735 |  |  |  |  |  |

| gat | gtg | ctt | gcc | aaa | gag | ctg | cag | ccc | cag | gcc | gac | agt | ggg | gac | agt | 2374 |
| Asp | Val | Leu | Ala | Lys | Glu | Leu | Gln | Pro | Gln | Ala | Asp | Ser | Gly | Asp | Ser |  |
| 740 |  |  |  |  | 745 |  |  |  |  | 750 |  |  |  |  | 755 |  |

| aaa | ctg | agt | cag | tgc | agc | tgc | tcc | acc | aat | ccc | agc | tct | ggc | caa | gag | 2422 |
| Lys | Leu | Ser | Gln | Cys | Ser | Cys | Ser | Thr | Asn | Pro | Ser | Ser | Gly | Gln | Glu |  |
|  |  |  |  | 760 |  |  |  |  | 765 |  |  |  |  | 770 |  |  |

| aaa | gac | ccc | aaa | att | aag | acc | gag | acg | aac | gag | gag | gta | tcg | gga | gac | 2470 |
| Lys | Asp | Pro | Lys | Ile | Lys | Thr | Glu | Thr | Asn | Glu | Glu | Val | Ser | Gly | Asp |  |
|  |  |  | 775 |  |  |  |  | 780 |  |  |  |  | 785 |  |  |  |

| ctg | gat | aat | cta | gat | gcc | att | ctt | gga | gat | ttg | acc | agt | tct | gac | ttc | 2518 |
| Leu | Asp | Asn | Leu | Asp | Ala | Ile | Leu | Gly | Asp | Leu | Thr | Ser | Ser | Asp | Phe |  |
|  |  | 790 |  |  |  |  | 795 |  |  |  |  | 800 |  |  |  |  |

| tac | aac | aat | cct | aca | aat | ggc | ggt | cac | cca | ggg | gcc | aaa | cag | cag | atg | 2566 |
| Tyr | Asn | Asn | Pro | Thr | Asn | Gly | Gly | His | Pro | Gly | Ala | Lys | Gln | Gln | Met |  |
|  | 805 |  |  |  |  | 810 |  |  |  |  | 815 |  |  |  |  |  |

| ttt | gca | gga | ccg | agt | tct | ctg | ggt | ttg | cga | agt | cca | cag | cct | gtg | cag | 2614 |
| Phe | Ala | Gly | Pro | Ser | Ser | Leu | Gly | Leu | Arg | Ser | Pro | Gln | Pro | Val | Gln |  |
| 820 |  |  |  |  | 825 |  |  |  |  | 830 |  |  |  |  | 835 |  |

| tct | gtt | cgt | cct | cca | tat | aac | cga | gcg | gtg | tct | ctg | gat | agc | cct | gtg | 2662 |
| Ser | Val | Arg | Pro | Pro | Tyr | Asn | Arg | Ala | Val | Ser | Leu | Asp | Ser | Pro | Val |  |
|  |  |  |  | 840 |  |  |  |  | 845 |  |  |  |  | 850 |  |  |

| tct | gtt | ggc | tca | ggt | ccg | cca | gtg | aag | aat | gtc | agt | gct | ttc | cct | ggg | 2710 |
| Ser | Val | Gly | Ser | Gly | Pro | Pro | Val | Lys | Asn | Val | Ser | Ala | Phe | Pro | Gly |  |
|  |  |  | 855 |  |  |  |  | 860 |  |  |  |  | 865 |  |  |  |

| tta | cca | aaa | cag | ccc | ata | ctg | gct | ggg | aat | cca | aga | atg | atg | gat | agt | 2758 |
| Leu | Pro | Lys | Gln | Pro | Ile | Leu | Ala | Gly | Asn | Pro | Arg | Met | Met | Asp | Ser |  |
|  |  | 870 |  |  |  |  | 875 |  |  |  |  | 880 |  |  |  |  |

| cag | gag | aat | tac | ggt | gcc | aac | atg | ggc | cca | aac | aga | aat | gtt | cct | gtg | 2806 |
| Gln | Glu | Asn | Tyr | Gly | Ala | Asn | Met | Gly | Pro | Asn | Arg | Asn | Val | Pro | Val |  |
|  | 885 |  |  |  |  | 890 |  |  |  |  | 895 |  |  |  |  |  |

| aat | ccg | act | tcc | tcc | ccc | gga | gac | tgg | ggc | tta | gct | aac | tca | agg | gcc | 2854 |
| Asn | Pro | Thr | Ser | Ser | Pro | Gly | Asp | Trp | Gly | Leu | Ala | Asn | Ser | Arg | Ala |  |
| 900 |  |  |  |  | 905 |  |  |  |  | 910 |  |  |  |  | 915 |  |

| agc | aga | atg | gag | cct | ctg | gca | tca | agt | ccc | ctg | gga | aga | act | gga | gcc | 2902 |
| Ser | Arg | Met | Glu | Pro | Leu | Ala | Ser | Ser | Pro | Leu | Gly | Arg | Thr | Gly | Ala |  |
|  |  |  |  | 920 |  |  |  |  | 925 |  |  |  |  | 930 |  |  |

| gat | tac | agt | gcc | act | tta | ccc | aga | cct | gcc | atg | ggg | ggc | tct | gtg | cct | 2950 |
| Asp | Tyr | Ser | Ala | Thr | Leu | Pro | Arg | Pro | Ala | Met | Gly | Gly | Ser | Val | Pro |  |
|  |  |  |  | 935 |  |  |  |  | 940 |  |  |  |  | 945 |  |  |

| acc | ttg | cca | ctt | cgt | tct | aat | cga | ctg | cca | ggt | gca | aga | cca | tcg | ttg | 2998 |

```
                                                                -continued

Thr Leu Pro Leu Arg Ser Asn Arg Leu Pro Gly Ala Arg Pro Ser Leu
        950                 955                 960 cag caa cag cag cag caa cag cag caa cag caa caa cag cag caa       3046
Gln Gln Gln Gln Gln Gln Gln Gln Gln Gln Gln Gln Gln Gln Gln
965                 970                 975 cag cag cag caa cag cag cag caa cag cag cag atg ctt caa atg       3094
Gln Gln Gln Gln Gln Gln Gln Gln Gln Gln Gln Met Leu Gln Met
    980                 985                 990                 995 aga act ggt gag att ccc atg gga atg gga gtc aat ccc tat agc cca   3142
Arg Thr Gly Glu Ile Pro Met Gly Met Gly Val Asn Pro Tyr Ser Pro
                1000                1005                1010 gca gtg ccg tct aac caa cca ggt tcc tgg cca gag ggc atg ctc tct   3190
Ala Val Pro Ser Asn Gln Pro Gly Ser Trp Pro Glu Gly Met Leu Ser
            1015                1020                1025 atg gaa caa ggt cct cac ggg tct caa aat agg cct ctt ctt aga aac   3238
Met Glu Gln Gly Pro His Gly Ser Gln Asn Arg Pro Leu Leu Arg Asn
        1030                1035                1040 tct ctg gat gat ctg ctt ggg cca cct tct aac gca gag ggc cag agt   3286
Ser Leu Asp Asp Leu Leu Gly Pro Pro Ser Asn Ala Glu Gly Gln Ser
    1045                1050                1055 gac gag aga gct ctg ctg gac cag ctg cac aca ctc ctg agc aac aca   3334
Asp Glu Arg Ala Leu Leu Asp Gln Leu His Thr Leu Leu Ser Asn Thr
1060                1065                1070                1075 gat gcc aca ggt ctg gag gag atc gac agg gcc ttg gga att cct gag   3382
Asp Ala Thr Gly Leu Glu Glu Ile Asp Arg Ala Leu Gly Ile Pro Glu
                1080                1085                1090 ctc gtg aat cag gga caa gct ttg gag tcc aaa cag gat gtt ttc caa   3430
Leu Val Asn Gln Gly Gln Ala Leu Glu Ser Lys Gln Asp Val Phe Gln
            1095                1100                1105 ggc caa gaa gca gca gta atg atg gat cag aag gct gca cta tat gga   3478
Gly Gln Glu Ala Ala Val Met Met Asp Gln Lys Ala Ala Leu Tyr Gly
        1110                1115                1120 cag aca tac cca gct cag ggt cct ccc ctt caa gga ggc ttt aac ctt   3526
Gln Thr Tyr Pro Ala Gln Gly Pro Pro Leu Gln Gly Gly Phe Asn Leu
    1125                1130                1135 cag gga cag tca cca tcg ttt aac tct atg atg ggt cag att agc cag   3574
Gln Gly Gln Ser Pro Ser Phe Asn Ser Met Met Gly Gln Ile Ser Gln
1140                1145                1150                1155 caa ggc agc ttt cct ctg caa ggc atg cat cct aga gcc ggc ctc gtg   3622
Gln Gly Ser Phe Pro Leu Gln Gly Met His Pro Arg Ala Gly Leu Val
                1160                1165                1170 aga cca agg acc aac acc ccg aag cag ctg aga atg cag ctt cag cag   3670
Arg Pro Arg Thr Asn Thr Pro Lys Gln Leu Arg Met Gln Leu Gln Gln
            1175                1180                1185 agg cta cag ggc cag cag ttt tta aat cag agc cgg cag gca ctt gaa   3718
Arg Leu Gln Gly Gln Gln Phe Leu Asn Gln Ser Arg Gln Ala Leu Glu
        1190                1195                1200 atg aaa atg gag aac cct gct ggc act gct gtg atg agg ccc atg atg   3766
Met Lys Met Glu Asn Pro Ala Gly Thr Ala Val Met Arg Pro Met Met
    1205                1210                1215 ccc cag gct ttc ttt aat gcc caa atg gct gcc cag cag aaa cga gag   3814
Pro Gln Ala Phe Phe Asn Ala Gln Met Ala Ala Gln Gln Lys Arg Glu
1220                1225                1230                1235 ctg atg agc cat cac ctg cag cag cag agg atg gcg atg atg atg tca   3862
Leu Met Ser His His Leu Gln Gln Gln Arg Met Ala Met Met Met Ser
                1240                1245                1250 caa cca cag cct cag gcc ttc agc cca cct ccc aac gtc acc gcc tcc   3910
Gln Pro Gln Pro Gln Ala Phe Ser Pro Pro Pro Asn Val Thr Ala Ser
            1255                1260                1265
```

| | | |
|---|---|---|
| ccc agc atg gac ggg gtt ttg gca ggt tca gca atg ccg caa gcc cct<br>Pro Ser Met Asp Gly Val Leu Ala Gly Ser Ala Met Pro Gln Ala Pro<br>    1270                        1275                   1280 | | 3958 |
| cca caa cag ttt cca tat cca gca aat tac gga atg gga caa cca cca<br>Pro Gln Gln Phe Pro Tyr Pro Ala Asn Tyr Gly Met Gly Gln Pro Pro<br>    1285                        1290                   1295 | | 4006 |
| gag cca gcc ttt ggt cga ggc tcg agt cct ccc agt gca atg atg tca<br>Glu Pro Ala Phe Gly Arg Gly Ser Ser Pro Ser Ala Met Met Ser<br>1300                 1305                   1310                   1315 | | 4054 |
| tca aga atg ggg cct tcc cag aat gcc atg gtg cag cat cct cag ccc<br>Ser Arg Met Gly Pro Ser Gln Asn Ala Met Val Gln His Pro Gln Pro<br>    1320                        1325                   1330 | | 4102 |
| aca ccc atg tat cag cct tca gat atg aag ggg tgg ccg tca ggg aac<br>Thr Pro Met Tyr Gln Pro Ser Asp Met Lys Gly Trp Pro Ser Gly Asn<br>            1335                        1340                   1345 | | 4150 |
| ctg gcc agg aat ggc tcc ttc ccc cag cag cag ttt gct ccc cag ggg<br>Leu Ala Arg Asn Gly Ser Phe Pro Gln Gln Gln Phe Ala Pro Gln Gly<br>    1350                        1355                   1360 | | 4198 |
| aac cct gca gcc tac aac atg gtg cat atg aac agc agc ggt ggg cac<br>Asn Pro Ala Ala Tyr Asn Met Val His Met Asn Ser Ser Gly Gly His<br>    1365                        1370                   1375 | | 4246 |
| ttg gga cag atg gcc atg acc ccc atg ccc atg tct ggc atg ccc atg<br>Leu Gly Gln Met Ala Met Thr Pro Met Pro Met Ser Gly Met Pro Met<br>1380                 1385                   1390                   1395 | | 4294 |
| ggc ccc gat cag aaa tac tgc tga catctcccta gtgggactga ctgtacagat<br>Gly Pro Asp Gln Lys Tyr Cys<br>            1400 | | 4348 |
| gacactgcac aggatcatca ggacgtggcg gcgagtcatt gtctaagcat ccagcttgga | | 4408 |
| aacaaggcca gcgtgaccag cagcggggtc tgtgctgtca tttgagcaga gctgggtctc | | 4468 |
| gctgaagcgc actgtctacc tgatgccctg cctctgtgtg gcaaggtgtt ctgcctcatg | | 4528 |
| aggatgtgat tctggagatg gggtgttcgt aagcaccgct ctcttacgtc actcccttct | | 4588 |
| gcctcgccag ccaaagtctt cacgtagatc tag | | 4621 |

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: forward
     primer A1B1/mESTF1 to screen mouse BAC

<400> SEQUENCE: 10
tccttttccc agcagcagtt tg                                               22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: reverse
     primer A1B1/mESTR1 used to screen mouse BAC

<400> SEQUENCE: 11
atgccagaca tgggcatggg                                                     20

<210> SEQ ID NO 12
<211> LENGTH: 1402
<212> TYPE: PRT
<213> ORGANISM: Mus musculus

<400> SEQUENCE: 12

-continued

```
Met Ser Gly Leu Gly Glu Ser Ser Leu Asp Pro Leu Ala Ala Glu Ser
 1               5                  10                  15

Arg Lys Arg Lys Leu Pro Cys Asp Ala Pro Gly Gln Gly Leu Val Tyr
            20                  25                  30

Ser Gly Glu Lys Trp Arg Arg Glu Gln Glu Ser Lys Tyr Ile Glu Glu
        35                  40                  45

Leu Ala Glu Leu Ile Ser Ala Asn Leu Ser Asp Ile Asp Asn Phe Asn
    50                  55                  60

Val Lys Pro Asp Lys Cys Ala Ile Leu Lys Glu Thr Val Arg Gln Ile
65                  70                  75                  80

Arg Gln Ile Lys Glu Gln Gly Lys Thr Ile Ser Ser Asp Asp Asp Val
                85                  90                  95

Gln Lys Ala Asp Val Ser Ser Thr Gly Gln Gly Val Ile Asp Lys Asp
            100                 105                 110

Ser Leu Gly Pro Leu Leu Leu Gln Ala Leu Asp Gly Phe Leu Phe Val
        115                 120                 125

Val Asn Arg Asp Gly Asn Ile Val Phe Val Ser Glu Asn Val Thr Gln
    130                 135                 140

Tyr Leu Gln Tyr Lys Gln Glu Asp Leu Val Asn Thr Ser Val Tyr Ser
145                 150                 155                 160

Ile Leu His Glu Gln Asp Arg Lys Asp Phe Leu Lys His Leu Pro Lys
                165                 170                 175

Ser Thr Val Asn Gly Val Ser Trp Thr Asn Glu Asn Gln Arg Gln Lys
            180                 185                 190

Ser His Thr Phe Asn Cys Arg Met Leu Met Lys Thr His Asp Ile Leu
        195                 200                 205

Glu Asp Val Asn Ala Ser Pro Glu Thr Arg Gln Arg Tyr Glu Thr Met
    210                 215                 220

Gln Cys Phe Ala Leu Ser Gln Pro Arg Ala Met Leu Glu Glu Gly Glu
225                 230                 235                 240

Asp Leu Gln Cys Cys Met Ile Cys Val Ala Arg Arg Val Thr Ala Pro
                245                 250                 255

Phe Pro Ser Ser Pro Glu Ser Phe Ile Thr Arg His Asp Leu Ser Gly
            260                 265                 270

Lys Val Val Asn Ile Asp Thr Asn Ser Leu Arg Ser Ser Met Arg Pro
        275                 280                 285

Gly Phe Glu Asp Ile Ile Arg Arg Cys Ile Gln Arg Phe Phe Ser Leu
    290                 295                 300

Asn Asp Gly Gln Ser Trp Ser Gln Lys Arg His Tyr Gln Glu Ala Tyr
305                 310                 315                 320

Val His Gly His Ala Glu Thr Pro Val Tyr Arg Phe Ser Leu Ala Asp
                325                 330                 335

Gly Thr Ile Val Ser Ala Gln Thr Lys Ser Lys Leu Phe Arg Asn Pro
            340                 345                 350

Val Thr Asn Asp Arg His Gly Phe Ile Ser Thr His Phe Leu Gln Arg
        355                 360                 365

Glu Gln Asn Gly Tyr Arg Pro Asn Pro Asn Pro Ala Gly Gln Gly Ile
    370                 375                 380

Arg Pro Pro Ala Ala Gly Cys Gly Val Ser Met Ser Pro Asn Gln Asn
385                 390                 395                 400

Val Gln Met Met Gly Ser Arg Thr Tyr Gly Val Pro Asp Pro Ser Asn
                405                 410                 415
```

-continued

```
Thr Gly Gln Met Gly Gly Ala Arg Tyr Gly Ala Ser Ser Val Ala
            420                 425             430

Ser Leu Thr Pro Gly Gln Ser Leu Gln Ser Pro Ser Tyr Gln Asn
            435                 440             445

Ser Ser Tyr Gly Leu Ser Met Ser Ser Pro Pro His Gly Ser Pro Gly
            450                 455             460

Leu Gly Pro Asn Gln Gln Asn Ile Met Ile Ser Pro Arg Asn Arg Gly
465             470                 475                 480

Ser Pro Lys Met Ala Ser His Gln Phe Ser Pro Ala Ala Gly Ala His
                485                 490                 495

Ser Pro Met Gly Pro Ser Gly Asn Thr Gly Ser His Ser Phe Ser Ser
            500                 505                 510

Ser Ser Leu Ser Ala Leu Gln Ala Ile Ser Glu Gly Val Gly Thr Ser
            515                 520                 525

Leu Leu Ser Thr Leu Ser Ser Pro Gly Pro Lys Leu Asp Asn Ser Pro
530             535                 540

Asn Met Asn Ile Ser Gln Pro Ser Lys Val Ser Gly Gln Asp Ser Lys
545                 550                 555                 560

Ser Pro Leu Gly Leu Tyr Cys Glu Gln Asn Pro Val Glu Ser Ser Val
                565                 570                 575

Cys Gln Ser Asn Ser Arg Asp His Pro Ser Glu Lys Glu Ser Lys Glu
                580                 585                 590

Ser Ser Gly Glu Val Ser Glu Thr Pro Arg Gly Pro Leu Glu Ser Lys
            595                 600                 605

Gly His Lys Lys Leu Leu Gln Leu Leu Thr Cys Ser Ser Asp Asp Arg
            610                 615             620

Gly His Ser Ser Leu Thr Asn Ser Pro Leu Asp Pro Asn Cys Lys Asp
625             630                 635                 640

Ser Ser Val Ser Val Thr Ser Pro Ser Gly Val Ser Ser Ser Thr Ser
                645                 650                 655

Gly Thr Val Ser Ser Thr Ser Asn Val His Gly Ser Leu Leu Gln Glu
            660                 665                 670

Lys His Arg Ile Leu His Lys Leu Leu Gln Asn Gly Asn Ser Pro Ala
            675                 680                 685

Glu Val Ala Lys Ile Thr Ala Glu Ala Thr Gly Lys Asp Thr Ser Ser
690                 695                 700

Thr Ala Ser Cys Gly Glu Gly Thr Thr Arg Gln Glu Gln Leu Ser Pro
705                 710                 715                 720

Lys Lys Lys Glu Asn Asn Ala Leu Leu Arg Tyr Leu Leu Asp Arg Asp
                725                 730                 735

Asp Pro Ser Asp Val Leu Ala Lys Glu Leu Gln Pro Gln Ala Asp Ser
                740                 745                 750

Gly Asp Ser Lys Leu Ser Gln Cys Ser Cys Ser Thr Asn Pro Ser Ser
                755                 760                 765

Gly Gln Glu Lys Asp Pro Lys Ile Lys Thr Glu Thr Asn Glu Glu Val
            770                 775                 780

Ser Gly Asp Leu Asp Asn Leu Asp Ala Ile Leu Gly Asp Leu Thr Ser
785                 790                 795                 800

Ser Asp Phe Tyr Asn Asn Pro Thr Asn Gly Gly His Pro Gly Ala Lys
                805                 810                 815

Gln Gln Met Phe Ala Gly Pro Ser Ser Leu Gly Leu Arg Ser Pro Gln
            820                 825                 830

Pro Val Gln Ser Val Arg Pro Pro Tyr Asn Arg Ala Val Ser Leu Asp
```

-continued

```
            835                 840                 845
Ser Pro Val Ser Val Gly Ser Gly Pro Pro Val Lys Asn Val Ser Ala
    850                 855                 860
Phe Pro Gly Leu Pro Lys Gln Pro Ile Leu Ala Gly Asn Pro Arg Met
865                 870                 875                 880
Met Asp Ser Gln Glu Asn Tyr Gly Ala Asn Met Gly Pro Asn Arg Asn
                885                 890                 895
Val Pro Val Asn Pro Thr Ser Ser Pro Gly Asp Trp Gly Leu Ala Asn
            900                 905                 910
Ser Arg Ala Ser Arg Met Glu Pro Leu Ala Ser Ser Pro Leu Gly Arg
            915                 920                 925
Thr Gly Ala Asp Tyr Ser Ala Thr Leu Pro Arg Pro Ala Met Gly Gly
        930                 935                 940
Ser Val Pro Thr Leu Pro Leu Arg Ser Asn Arg Leu Pro Gly Ala Arg
945                 950                 955                 960
Pro Ser Leu Gln Gln Gln Gln Gln Gln Gln Gln Gln Gln Gln Gln Gln
                965                 970                 975
Gln Gln Gln Gln Gln Gln Gln Gln Gln Gln Gln Gln Gln Gln Gln Met
            980                 985                 990
Leu Gln Met Arg Thr Gly Glu Ile Pro Met Gly Met Gly Val Asn Pro
        995                 1000                1005
Tyr Ser Pro Ala Val Pro Ser Asn Gln Pro Gly Ser Trp Pro Glu Gly
    1010                1015                1020
Met Leu Ser Met Glu Gln Gly Pro His Gly Ser Gln Asn Arg Pro Leu
1025                1030                1035                1040
Leu Arg Asn Ser Leu Asp Asp Leu Leu Gly Pro Pro Ser Asn Ala Glu
                1045                1050                1055
Gly Gln Ser Asp Glu Arg Ala Leu Leu Asp Gln Leu His Thr Leu Leu
            1060                1065                1070
Ser Asn Thr Asp Ala Thr Gly Leu Glu Glu Ile Asp Arg Ala Leu Gly
        1075                1080                1085
Ile Pro Glu Leu Val Asn Gln Gly Gln Ala Leu Glu Ser Lys Gln Asp
    1090                1095                1100
Val Phe Gln Gly Gln Glu Ala Ala Val Met Met Asp Gln Lys Ala Ala
1105                1110                1115                1120
Leu Tyr Gly Gln Thr Tyr Pro Ala Gln Gly Pro Pro Leu Gln Gly Gly
                1125                1130                1135
Phe Asn Leu Gln Gly Gln Ser Pro Ser Phe Asn Ser Met Met Gly Gln
            1140                1145                1150
Ile Ser Gln Gln Gly Ser Phe Pro Leu Gln Gly Met His Pro Arg Ala
        1155                1160                1165
Gly Leu Val Arg Pro Arg Thr Asn Thr Pro Lys Gln Leu Arg Met Gln
    1170                1175                1180
Leu Gln Gln Arg Leu Gln Gly Gln Gln Phe Leu Asn Gln Ser Arg Gln
1185                1190                1195                1200
Ala Leu Glu Met Lys Met Glu Asn Pro Ala Gly Thr Ala Val Met Arg
                1205                1210                1215
Pro Met Met Pro Gln Ala Phe Phe Asn Ala Gln Met Ala Ala Gln Gln
            1220                1225                1230
Lys Arg Glu Leu Met Ser His His Leu Gln Gln Arg Met Ala Met
        1235                1240                1245
Met Met Ser Gln Pro Gln Pro Gln Ala Phe Ser Pro Pro Asn Val
    1250                1255                1260
```

```
Thr Ala Ser Pro Ser Met Asp Gly Val Leu Ala Gly Ser Ala Met Pro
1265                1270                1275                1280

Gln Ala Pro Pro Gln Gln Phe Pro Tyr Pro Ala Asn Tyr Gly Met Gly
            1285                1290                1295

Gln Pro Pro Glu Pro Ala Phe Gly Arg Gly Ser Ser Pro Pro Ser Ala
            1300                1305                1310

Met Met Ser Ser Arg Met Gly Pro Ser Gln Asn Ala Met Val Gln His
        1315                1320                1325

Pro Gln Pro Thr Pro Met Tyr Gln Pro Ser Asp Met Lys Gly Trp Pro
    1330                1335                1340

Ser Gly Asn Leu Ala Arg Asn Gly Ser Phe Pro Gln Gln Gln Phe Ala
1345                1350                1355                1360

Pro Gln Gly Asn Pro Ala Ala Tyr Asn Met Val His Met Asn Ser Ser
            1365                1370                1375

Gly Gly His Leu Gly Gln Met Ala Met Thr Pro Met Pro Met Ser Gly
            1380                1385                1390

Met Pro Met Gly Pro Asp Gln Lys Tyr Cys
        1395                1400
```